(12) United States Patent
Wallberg et al.

(10) Patent No.: US 7,678,796 B2
(45) Date of Patent: Mar. 16, 2010

(54) MGLUR5 MODULATORS I

(75) Inventors: Andreas Wallberg, Mölndal (SE);
Karolina Nilsson, Mölndal (SE); Björn Holm, Mölndal (SE); Mats Nagard, Molndal (SE); Kenneth Granberg, Molndal (SE); Abdelmalik Slassi, Mississauga (CA); Louise Edwards, Mississauga (CA); Methvin Isaac, Brampton (CA); Tao Xin, Toronto (CA); Tomislav Stefanac, Burlington (CA)

(73) Assignee: AstraZeneca AB, Sodertalje (SE)

( * ) Notice: Subject to any disclaimer, the term of this patent is extended or adjusted under 35 U.S.C. 154(b) by 28 days.

(21) Appl. No.: 11/790,417

(22) Filed: Apr. 25, 2007

(65) Prior Publication Data

US 2007/0259862 A1    Nov. 8, 2007

Related U.S. Application Data

(60) Provisional application No. 60/797,659, filed on May 5, 2006.

(51) Int. Cl.
| | |
|---|---|
| A61K 31/541 | (2006.01) |
| A61K 31/5377 | (2006.01) |
| A61K 31/513 | (2006.01) |
| A61K 31/497 | (2006.01) |
| A61K 31/496 | (2006.01) |
| A61K 31/501 | (2006.01) |
| C07D 413/02 | (2006.01) |
| C07D 417/14 | (2006.01) |
| A61P 1/00 | (2006.01) |

(52) U.S. Cl. ............ 514/252.05; 514/255.05; 514/256; 514/269; 514/274; 514/343; 514/252.19; 514/252.02; 514/252.03; 514/247; 514/346; 514/751; 514/546; 544/238; 544/315; 544/319; 544/333; 544/405; 544/295; 544/310; 544/390; 544/312; 544/224; 544/239; 546/269.1; 546/272.1; 546/272.4; 546/291; 548/532; 548/537; 548/247; 548/131; 548/254; 548/267.2; 560/254; 570/128

(58) Field of Classification Search ............ 514/252.05, 514/255.05, 256, 269, 274, 340; 544/238, 544/315, 319, 333, 405; 546/269.1, 272.1, 546/272.4

See application file for complete search history.

(56) References Cited

FOREIGN PATENT DOCUMENTS

| WO | WO-2004-014370 A2 | 2/2004 |
|---|---|---|
| WO | WO-2004-014881 A2 | 2/2004 |
| WO | WO-2004-014902 A2 | 2/2004 |
| WO | WO-2005-044797 A1 | 5/2005 |
| WO | WO-2005-077345 A1 | 8/2005 |
| WO | WO-2005-077368 A2 | 8/2005 |
| WO | WO-2005-077373 A2 | 8/2005 |
| WO | WO-2005-080356 A1 | 9/2005 |
| WO | WO-2005-080386 A1 | 9/2005 |
| WO | WO-2005-080397 A1 | 9/2005 |
| WO | WO-2006-014185 A1 | 2/2006 |
| WO | WO-2006/048771 A | 5/2006 |
| WO | WO-2007-006530 A1 | 1/2007 |

OTHER PUBLICATIONS

Brittain, Chapter V, Polymorphism in Pharmaceutical Solids, 1999, pp. 126-127.*
Schoepp et al., Trends Pharmacol. Sci. 14:13 (1993).
Schoepp, Neurochem. Int. 24(5):439 (1994).
Pin et al., Neuropharmacology 34(1):1 (1995).
Bordi and Ugolini, Prog. Neurobiol. 59:55 (1999).
Nakanishi, Neuron 13: 1031 (1994).
Knopfel et al., J. Med. Chem. 38(9):1417 (1995).
Pin et al., PNAS 89:10331 (1992).
Minakami et al., BBRC 199(3):1136 (1994).
Joly et al., J. Neurosci. 15(5):3970 (1995).
Baskys, Trends Pharmacol. Sci. 15(3):92 (1992).
Watkins et al., Trends Pharmacol. Sci. 15:333 (1994).
Bashir et al., Nature 363:347 (1993).
Bortolotto et al., Nature 368:740 (1994).
Aiba et al., Cell 79:377 (1994).
Aiba et al. Cell 79:365 (1994).
Meller et al., Neuroreport 4: 879 (1993).
Bordi and Ugolini, Brain Res. 871:223 (2000).
Cunningham et al., Life Sci. 54:135 (1994).
Hollman et al., Ann. Rev. Neurosci. 17:31 (1994).
Spooren et al., Trends Pharmacol. Sci. 22(7):331 (2001).
Gasparini et al., Curr. Opin. Pharmacol. 2:43 (2002).
Neugebauer Pain 98:1 (2002).
Holloway & Dent (1990) Gastroenterol. Clin. N. Amer. 19(3), pp. 517-535.
Vandenberg et al., hERG K+ channels: friend and foe. Trends Pharmacol Sci 2001; 22: 240-246.
Mittal et al., "Transient Lower Esophageal Sphincter Relaxation", Gastroenterology, 1995, 109, pp. 601-610.
van Herwaarden et al., "Diagnosis of Reflux Disease", Baillière's Clinical Gastroenterology, 2000, vol. 14, No. 5, pp. 759-774.

* cited by examiner

*Primary Examiner*—Mark L Berch
*Assistant Examiner*—Cecilia M Jaisle
(74) *Attorney, Agent, or Firm*—Birch, Stewart, Kolasch & Birch, LLP

(57) ABSTRACT

The present invention is directed to novel compounds, to a process for their preparation, their use in therapy and pharmaceutical compositions comprising the novel compounds.

21 Claims, No Drawings

MGLUR5 MODULATORS I

This Nonprovisional application claims priority under 35 U.S.C. § 119(e) on U.S. Provisional Application No(s). 60/797,659 filed on May 5, 2006, the entire contents of which are hereby incorporated by reference.

FIELD OF THE INVENTION

The present invention is directed to novel compounds, their use in therapy and pharmaceutical compositions comprising said novel compounds.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Molecular cloning has identified eight distinct mGluR subtypes, termed mGluR1 through mGluR8. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Neurological, Psychiatric and Pain Disorders

Attempts at elucidating the physiological roles of Group I mGluRs suggest that activation of these receptors elicits neuronal excitation. Various studies have demonstrated that Group I mGluR agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1 (1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated, Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13:1031 (1994), Pin et al., *Neuropharmacology* 34:1, Knopfel et al., *J Med. Chem.* 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Gastrointestinal Disorders

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent (1990) *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

The novel compounds according to the present invention are assumed to be useful for the inhibition of transient lower esophageal sphincter relaxations (TLESRs) and thus for treatment of gastro-esophageal reflux disorder (GERD).

It is well known that certain compounds may cause undesirable effects on cardiac repolarisation in man, observed as a prolongation of the QT interval on electrocardiograms (ECG). In extreme circumstances, this drug-induced prolongation of the QT interval can lead to a type of cardiac arrhythmia called Torsades de Pointes (TdP; Vandenberg et al. hERG K$^+$ channels: friend and foe. Trends Pharmacol Sci 2001; 22: 240-246), leading ultimately to ventricular fibrillation and sudden death. The primary event in this syndrome is inhibition of the rapid component of the delayed rectifying potassium current (IKr) by these compounds. The compounds bind to the aperture-forming alpha sub-units of the channel protein carrying this current—sub-units that are encoded by the human ether-a-go-go-related gene (hERG). Since IKr plays a key role in repolarisation of the cardiac action potential, its inhibition slows repolarisation and this is manifested as a prolongation of the QT interval. Whilst QT interval prolongation is not a safety concern per se, it carries a risk of cardiovascular adverse effects and in a small percentage of people it can lead to TdP and degeneration into ventricular fibrillation.

Generally, compounds of the present invention have low activity against the hERG-encoded potassium channel. In this regard, low activity against hERG in vitro is indicative of low activity in vivo.

It is also desirable for drugs to possess good metabolic stability in order to enhance drug efficacy. Stability against human microsomal metabolism in vitro is indicative of stability towards metabolism in vivo.

Because of their physiological and pathophysiological significance, there is a need for new potent mGluR agonists and antagonists that display a high selectivity for mGluR subtypes, particularly the Group I receptor subtype, most particularly the mGluR5.

The object of the present invention is to provide compounds exhibiting an activity at metabotropic glutamate receptors (mGluRs), especially at the mGluR5 receptor. In particular, the compounds according to the present invention are predominantly peripherally acting, i.e. have a limited ability of passing the blood-brain barrier.

DESCRIPTION OF THE INVENTION

The present invention relates to a compound of formula I:

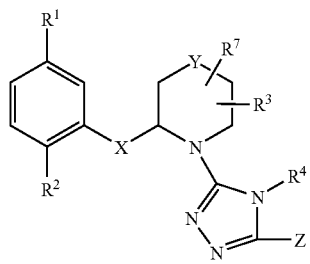

(I)

wherein
$R^1$ is methyl, halogen or cyano;
$R^2$ is hydrogen or fluoro;
$R^3$ is hydrogen, fluoro or $C_1$-$C_3$ alkyl;
$R^4$ is $C_1$-$C_3$ alkyl or cyclopropyl;
Y is bond, $CR^8$, O, S, SO, $SO_2$, or $NR^9$;
X is

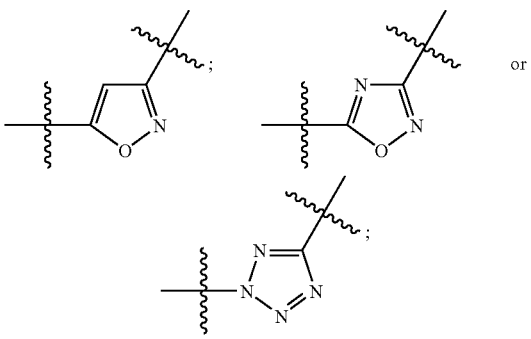

and Z is

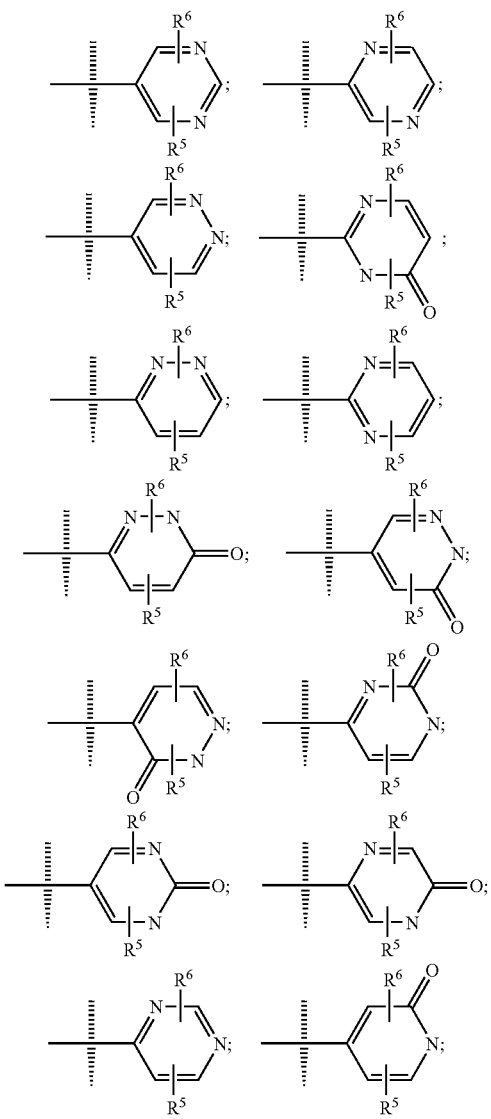

-continued

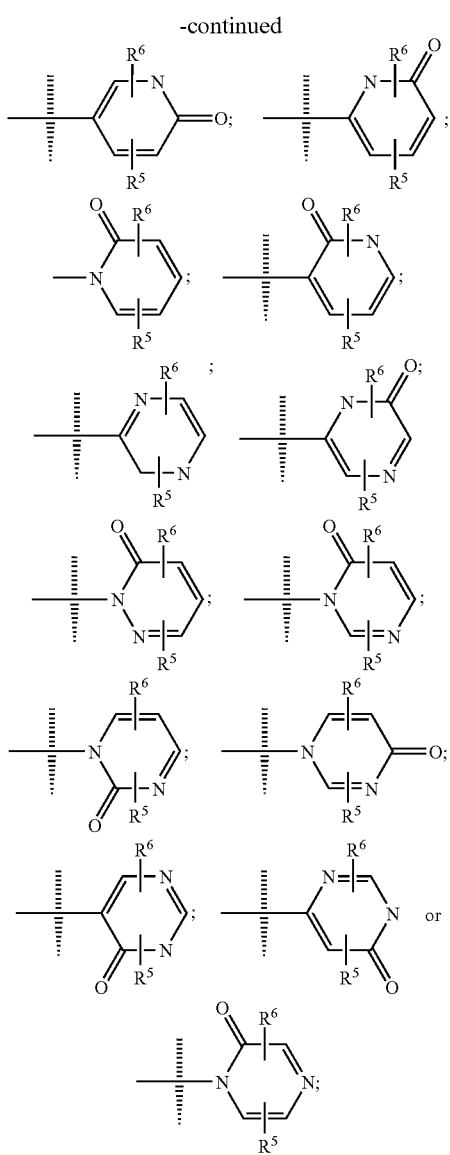

wherein
$R^5$ is hydrogen, $C_1$-$C_3$ alkyl, $C_1$-$C_3$ haloalkyl, $C_1$-$C_3$ alkoxy; $C_1$-$C_3$ haloalkoxy; or halogen;
$R^6$ is hydrogen, $C_1$-$C_3$ alkyl, $C_1$-$C_3$ haloalkyl, $C_1$-$C_3$ alkoxy; $C_1$-$C_3$ haloalkoxy; or halogen;
$R^7$ is hydrogen, fluoro or $C_1$-$C_3$ alkyl;
$R^8$ is hydrogen, fluoro or $C_1$-$C_3$ alkyl;
$R^9$ is hydrogen or $C_1$-$C_3$ alkyl;

as well as pharmaceutically acceptable salts, hydrates, isoforms, tautomers and/or enantiomers thereof.

In one embodiment $R^1$ is halogen or cyano.
In a further embodiment, $R^1$ is chloro. In a further embodiment, $R^1$ is fluoro. In a further embodiment, $R^1$ is cyano. In a further embodiment, $R^1$ is methyl.
In a further embodiment, $R^2$ is hydrogen.
In a further embodiment, $R^3$ is hydrogen or fluoro.
In a further embodiment, $R^4$ is $C_1$-$C_2$ alkyl.
In a further embodiment, $R^4$ is methyl.
In a further embodiment, $R^5$ is hydrogen, $C_1$-$C_2$ alkyl or $C_1$-$C_2$ alkoxy.

In a further embodiment, $R^6$ is hydrogen, $C_1$-$C_2$ alkyl or $C_1$-$C_2$ alkoxy.
In a further embodiment, $R^7$ is hydrogen or fluoro.
In a further embodiment, Y is a bond.
In a further embodiment, Y is C.
In a further embodiment, Z is

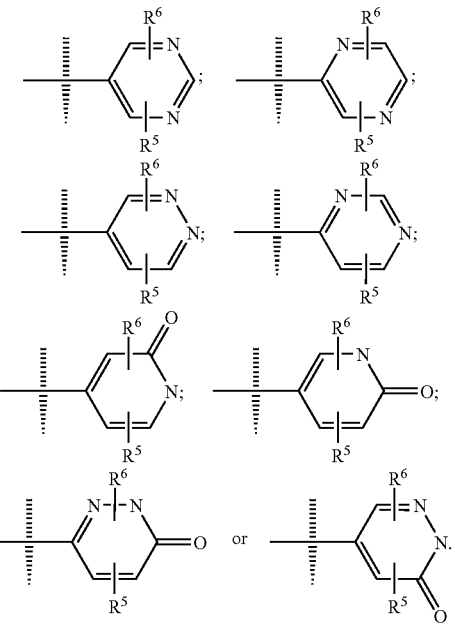

Another embodiment is a pharmaceutical composition comprising as active ingredient a therapeutically effective amount of the compound according to formula I, in association with one or more pharmaceutically acceptable diluents, excipients and/or inert carriers.

Other embodiments, as described in more detail below, relate to a compound according to formula I for use in therapy, in treatment of mGluR5 mediated disorders, in the manufacture of a medicament for the treatment of mGluR5 mediated disorders.

Still other embodiments relate to a method of treatment of mGluR5 mediated disorders, comprising administering to a mammal a therapeutically effective amount of the compound according to formula I.

In another embodiment, there is provided a method for inhibiting activation of mGluR5 receptors, comprising treating a cell containing said receptor with an effective amount of the compound according to I.

The compounds of the present invention are useful in therapy, in particular for the treatment of neurological, psychiatric, pain, and gastrointestinal disorders.

It will also be understood by those of skill in the art that certain compounds of the present invention may exist in solvated, for example hydrated, as well as unsolvated forms. It will further be understood that the present invention encompasses all such solvated forms of the compounds of formula I.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl, acetic acid or a methanesulfonic acid to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The general terms used in the definition of formula I have the following meanings:

Halogen as used herein is selected from chlorine, fluorine, bromine or iodine.

$C_1$-$C_3$ alkyl is a straight or branched alkyl group, having from 1 to 3 carbon atoms, for example methyl, ethyl, n-propyl or isopropyl.

$C_1$-$C_3$ alkoxy is an alkoxy group having 1 to 3 carbon atoms, for example methoxy, ethoxy, isopropoxy or n-propoxy.

$C_1$-$C_3$ haloalkoxy is an alkoxy group having 1 to 3 carbon atoms, for example methoxy, ethoxy or n-propoxy wherein at least one of the carbon atoms is substituted by a halogen atom.

All chemical names were generated using a software known as AutoNom accessed through ISIS draw.

In formula I above, X may be present in any of the two possible orientations.

Pharmaceutical Composition

The compounds of the present invention may be formulated into conventional pharmaceutical compositions comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, or from about 0.10% w to 50% w, of a compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

The compounds according to the present invention are useful in the treatment of conditions associated with excitatory activation of mGluR5 and for inhibiting neuronal damage caused by excitatory activation of mGluR5. The compounds may be used to produce an inhibitory effect of mGluR5 in mammals, including man.

The Group I mGluR receptors including mGluR5 are highly expressed in the central and peripheral nervous system and in other tissues. Thus, it is expected that the compounds of the invention are well suited for the treatment of mGluR5-mediated disorders such as acute and chronic neurological and psychiatric disorders, gastrointestinal disorders, and chronic and acute pain disorders.

The invention relates to compounds of formula I, as defined hereinbefore, for use in therapy.

The invention relates to compounds of formula I, as defined hereinbefore, for use in treatment of mGluR5-mediated disorders.

The invention relates to compounds of formula I, as defined hereinbefore, for use in treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, opthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of formula I, as defined above, for use in treatment of pain related to migraine, inflammatory pain, neuropathic pain disorders such as diabetic neuropathies, arthritis and rheumatiod diseases, low back pain, post-operative pain and pain associated with various conditions including cancer, angina, renal or billiary colic, menstruation, migraine and gout.

The invention relates to compounds of formula I as defined hereinbefore, for use in treatment of stroke, head trauma, anoxic and ischemic injuries, hypoglycemia, cardiovascular diseases and epilepsy.

The present invention relates also to the use of a compound of formula I as defined hereinbefore, in the manufacture of a medicament for the treatment of mGluR Group I receptor-mediated disorders and any disorder listed above.

One embodiment of the invention relates to the use of a compound according to formula I in the treatment of gastrointestinal disorders.

Another embodiment of the invention relates to the use of a formula I compound for the manufacture of a medicament for inhibition of transient lower esophageal sphincter relaxations, for the treatment of GERD, for the prevention of gastroesophageal reflux, for the treatment regurgitation, for treatment of asthma, for treatment of laryngitis, for treatment of lung disease, for the management of failure to thrive, for the treatment of irritable bowel disease (IBS) and for the treatment of functional dyspepsia (FD).

Another embodiment of the present invention relates to the use of a compound of formula I for treatment of overactive bladder or urinary incontinence.

The wording "TLESR", transient lower esophageal sphincter relaxations, is herein defined in accordance with Mittal, R. K, Holloway, R. H., Penagini, R., Blackshaw, L. A., Dent, J, 1995; *Transient lower esophageal sphincter relaxation, Gastroenterology* 109, pp. 601-610.

The wording "reflux" is herein defined as fluid from the stomach being able to pass into the esophagus, since the mechanical barrier is temporarily lost at such times.

The wording "GERD", gastro-esophageal reflux disease, is herein defined in accordance with van Heerwarden, M A., Smout A. J. P. M, 2000; *Diagnosis of reflux disease. Baillière's Clin. Gastroenterol,* 14, pp. 759-774.

The compounds of formula I above are useful for the treatment or prevention of obesity or overweight, (e.g., promotion of weight loss and maintenance of weight loss), prevention or reversal of weight gain (e.g., rebound, medication-induced or subsequent to cessation of smoking), for modulation of appetite and/or satiety, eating disorders (e.g. binge eating, anorexia, bulimia and compulsive) and cravings (for drugs, tobacco, alcohol, any appetizing macronutrients or non-essential food items).

The invention also provides a method of treatment of mGluR5-mediated disorders and any disorder listed above, in a patient suffering from, or at risk of, said condition, which comprises administering to the patient an effective amount of a compound of formula I, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly.

In this specification, unless stated otherwise, the term "antagonist" and "inhibitor" shall mean a compound that by any means, partly or completely, blocks the transduction pathway leading to the production of a response by the ligand.

The term "disorder", unless stated otherwise, means any condition and disease associated with metabotropic glutamate receptor activity.

One embodiment of the present invention is a combination of a compound of formula I and an acid secretion inhibiting agent. A "combination" according to the invention may be present as a "fix combination" or as a "kit of parts combination". A "fix combination" is defined as a combination wherein the (i) at least one acid secretion inhibiting agent; and (ii) at least one compound of formula I are present in one unit. A "kit of parts combination" is defined as a combination wherein the (i) at least one acid secretion inhibiting agent; and (ii) at least one compound of formula I are present in more than one unit. The components of the "kit of parts combination" may be administered simultaneously, sequentially or separately. The molar ratio of the acid secretion inhibiting agent to the compound of formula I used according to the invention in within the range of from 1:100 to 100:1, such as from 1:50 to 50:1 or from 1:20 to 20:1 or from 1:10 to 10:1. The two drugs may be administered separately in the same ratio. Examples of acid secretion inhibiting agents are H2 blocking agents, such as cimetidine, ranitidine; as well as proton pump inhibitors such as pyridinylmethylsulfinyl benzimidazoles such as omeprazole, esomeprazole, lansoprazole, pantoprazole, rabeprazole or related substances such as leminoprazole.

Non-Medical Use

In addition to their use in therapeutic medicine, the compounds of formula I, as well as salts and hydrates of such compounds, are useful as pharmacological tools in the development and standardisation of in vitro and in vivo test systems for the evaluation of the effects of inhibitors of mGluR related activity in laboratory animals such as cats, dogs, rabbits, monkeys, rats and mice, as part of the search for new therapeutic agents.

Methods of Preparation

Another aspect of the present invention provides processes for preparing compounds of formula I, or salts or hydrates thereof. Processes for the preparation of the compounds in the present invention are described herein.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C.

The term "reflux" shall mean, unless otherwise stated, in reference to an employed solvent a temperature at or above the boiling point of named solvent.

Abbreviations
atm Atmosphere
aq. Aqueous
BINAP 2,2'-bis(diphenylphosphino)-1,1'-binaphthyl
Boc tert-butoxycarbonyl
CDI N,N'-Carbonyldiimidazole
DCC N,N-Dicyclohexylcarbodiimide
DCM Dichloromethane
DBU Diaza(1,3)bicyclo[5.4.0]undecane
DEA N,N-Diisopropyl ethylamine
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
EA Ethyl acetate
EDCI N-[3-(dimethylamino)propyl]-N'-ethylcarbodiimide hydrochloride
EDC 1-Ethyl-3-(3-dimethylaminopropyl)carbodiimide
Et$_2$O Diethylether
EtOAc Ethyl acetate
EtOH Ethanol
EtI Iodoethane
Et Ethyl
Fmoc 9-fluorenylmethyloxycarbonyl
h hour(s)
HetAr Heteroaryl
HOBt N-Hydroxybenzotriazole
HBTU O-(Benzotriazol-1-yl)-N,N,N',N'-tetramethyluronium hexafluorophosphate
HPLC High performance liquid chromatography
LAH Lithium aluminium hydride
LCMS HPLC mass spec
MCPBA m-Chlorbenzoic acid
MeCN Acetonitrile
MeOH Methanol
min Minutes
MeI Iodomethane
MeMgCl Methyl magnesium chloride
Me Methyl
n-BuLi 1-Butyllithium
NaOAc Sodium acetate
NMR Nuclear magnetic resonance
NMP N-Methyl pyrrolidinone
nBuLi 1-Butyl lithium
o.n. Over night
RT, rt, r.t. Room temperature
TEA Triethylamine
THF Tetrahydrofurane
nBu normal Butyl
OMs Mesylate or methane sulfonate ester
OTs Tosylate, toluene sulfonate or 4-methylbenzene sulfonate ester
MTBE Methyl, tertbutyl ether
PCC Pyridinium chlorochromate
PPTS Pyridinium p-toluenesulfonate
TBAF Tetrabutylammonium fluoride
pTsOH p-Toluenesulfonic acid
SPE Solid phase extraction (usually containing silica gel for mini-chromatography)
sat. Saturated Preparation of Intermediates The intermediates provided in synthetic paths given below, are useful for further preparation of compounds of formula I. Other starting materials are either commercially available or can be prepared via methods described in the literature. The synthetic pathways described below are non-limiting examples of preparations that can be used. One of skill in the art would understand other pathways might be used.

Synthesis of Isoxazoles

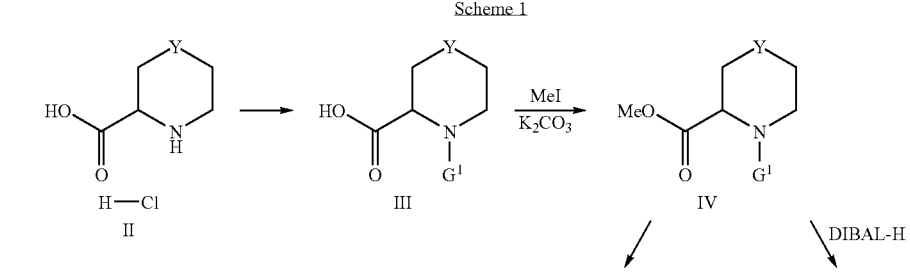

Scheme 1

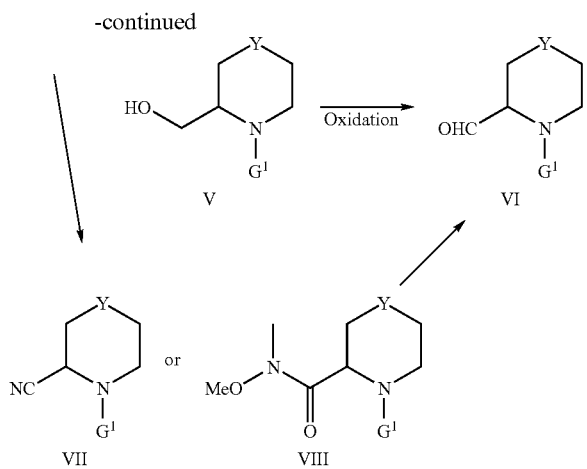

Aldehydes of formula VI wherein Y is as defined in formula I may be used in the preparation of isoxazoles. Commercially available acid derivatives of formula II wherein Y is bond C, S, SO, $SO_2$, N—R(R is either $R^3$ or $R^7$ as defined in formula I) and N-$G^2$ ($G^2$ is a protecting group orthogonal to $G^1$) may undergo N-protection to yield compounds of formula III wherein $G^1$ is a protecting group such as Boc or Fmoc using methods well known in the art. The acid moiety in compounds of formula III may be transformed into an alkyl ester of formula IV, such as for example the methyl or ethyl ester, which may be transformed to aldehydes of formula VI using a mild reducing agent such as DIBAL-H in a solvent such as toluene at low temperature, for example −78° C. Higher temperatures or stronger reducing agents may result in formation of the primary alcohols of formula V, either exclusively or as a mixture with the aldehydes of formula VI. Other functional groups such as the primary alcohol in compounds of formula V, the nitrile in compounds of formula VII and Weinreb amide moiety in compounds of formula VIII may be transformed into aldehydes of formula VI utilizing procedures established in the art. Additionally, acids of formula II may be converted into nitriles of formula VII by methods known in the art, for example by conversion of the acid to the primary amide followed by dehydration to the nitrile.

Aldehydes of formula VI may be converted to oximes of formula IX by treatment with hydroxylamine, in a solvent such as pyridine, at a temperature between 0° C. to room temperature, scheme 2. Isoxazoles of formula X may be prepared by chlorination of oximes of formula IX using a reagent such as N-chlorosuccinimide (NCS), followed by 1,3-dipolar cycloaddition with the appropriately R-substituted acetylenes, wherein R may be an aryl, substituted aryl or a masking group (eg. alkyl stannane) (Steven, R. V. et al. *J. Am. Chem. Soc.* 1986, 108, 1039). The isoxazole intermediate X can subsequently be deprotected to give XI by standard methods.

Scheme 2

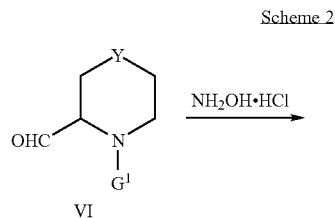

Isoxazoles of formula X wherein R is a masking group may be prepared in this manner and the masking group transformed into the desired R group by cross-coupling reactions. For example, the use of trialkylstannylacetylenes would result in a trialkylstannyl isoxazole which may undergo reactions such as for example Stille type cross coupling to introduce aryl substituents by coupling to an appropriate aryl halide.

Synthesis of [1,2,4]-Oxadiazoles

Scheme 3

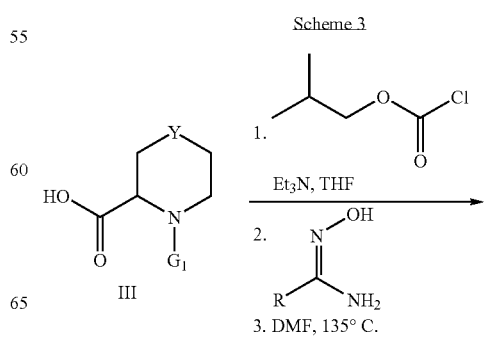

-continued

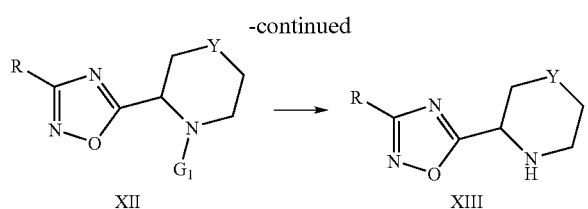

XII → XIII

Carboxylic acids of formula III may be used in the preparation of the corresponding 3-R substituted [1,2,4]oxadiazoles of formula XII by activation of the acid moiety, addition of a suitable R-substituted hydroxyamidine to form an ester, followed by cyclization to the oxadiazole XIII. [See Tetrahedron Lett., 2001, 42, 1495-98, Tetrahedron Lett., 2001, 42, 1441-43, and Bioorg. Med. Chem. Lett. 1999, 9, 1869-74]. The acid may be activated as the mixed anhydride using an alkyl chloroformate such as isobutyl chloroformate, in the presence of a base such as triethylamine in a suitable solvent such as THF. Alternatively, other well known methods of activating the acid may be employed, including in situ activation of the acid using a reagent such as EDCI, DCC, DIC or HBTU, with or without the presence of co-reagents such as HOBt or DMAP, in suitable solvents such as DMF, DCM, THF, or MeCN at a temperature from −20 to 100° C. The cyclization may be accomplished by heating in a solvent such as pyridine or DMF, under microwave irradiation or by employing catalysts such as TBAF. R-substituted hydroxyamidines are available from nitriles by addition of hydroxylamine hydrochloride in the presence of a base such as NaOH, NaHCO$_3$ or Na$_2$CO$_3$, to generate the free hydroxylamine, in a solvent such as ethanol or methanol or the like, at temperatures between room temperature and 100° C.

Synthesis of Tetrazoles

Scheme 4

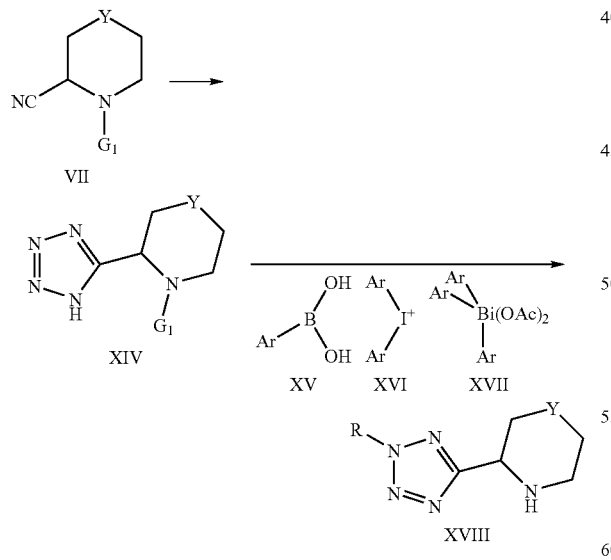

Nitriles of formula VII may be used in the preparation of the corresponding tetrazoles of formula XVIII by treatment with an azide, such as NaN$_3$, LiN$_3$, trialkylyltinazide or trimethylsilylazide, preferably with a catalyst such as dibutyltin oxide or ZnBr$_2$, in solvents such as DMF, water or toluene at a temperature of 50 to 200° C. by conventional heating or microwave irradiation [See J. Org. Chem. 2001, 7945-7950; J. Org. Chem. 2000, 7984-7989 or J. Org. Chem. 1993, 4139-4141].

N2-arylation of 5-substituted tetrazoles have been reported in the literature using a variety of coupling partners. Compounds of formula XVIII wherein R is an aryl group may be prepared using for example boronic acids of formula XV [with the B(OH)$_2$ moiety], or the corresponding iodonium salts of formula XVII [with the I$^+$—Ar moiety], or the corresponding triarylbismuth diacetates [with the Bi(OAc)$_2$Ar$_2$ moiety], as arylating agents mediated by transition metals [See Tetrahedron Lett. 2002, 6221-6223; Tetrahedron Lett. 1998, 2941-2944; Tetrahedron Lett. 1999, 2747-2748]. With boronic acids, stoichiometric amounts of Cu(II) acetate and pyridine are used in solvents such as dichloromethane, DMF, dioxane or THF at a temperature of room temperature to 100° C. With iodonium salts, catalytic amounts of Pd(II)-compounds, such as Pd(OAc)$_2$ or a Pd(0) complex such as Pd(dba)$_2$ or, together with catalytic amounts of Cu(II)-carboxylates, such as Cu(II)-phenylcyclopropylcarboxylate, and bidentate ligands, such as BINAP or DPPF, are used in solvents such as t-BuOH at a temperature of 50 to 100° C. With triarylbismuth diacetates, catalytic amounts of cupric acetate may be employed in the presence of N,N,N',N'-tetramethylguanidine in a suitable solvent such as THF with heating at a temperature of 40-60° C. Iodonium salts of formula XVI may be obtained from, for example, the respective boronic acids by treatment with hypervalent iodine substituted aromatics, such as hydroxyl(tosyloxy)iodobenzene or PhI(OAc)$_2$×2TfOH, in dichloromethane or the like [See Tetrahedron Lett. 2000, 5393-5396]. Triarylbismuth diacetates may be prepared from aryl magnesium bromides with bismuth trichloride in a suitable solvent such as refluxing THF to give the triarylbismuthane, which is then oxidized to the diacetate using an oxidizing agent such as sodium perborate in acetic acid [Synth. Commun. 1996, 4569-75].

Synthesis of Amino-Triazoles

Scheme 5

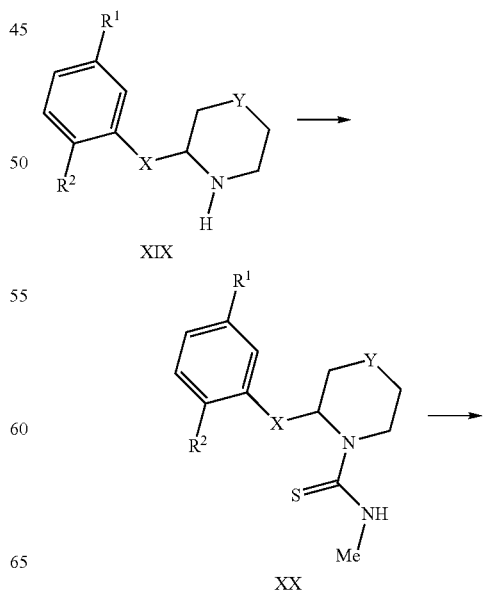

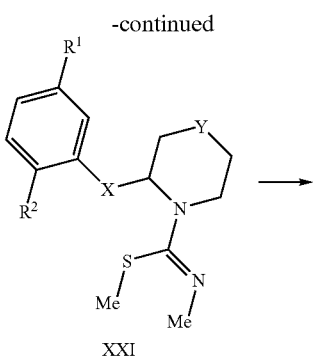

XXI

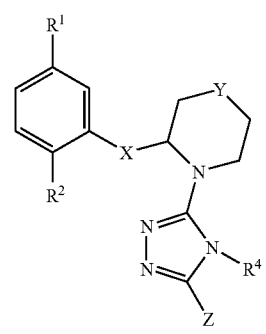

Formula I

The deprotected amines of formula XI, XIII, XVIII and XIX may be subjected to a sequence of thiourea formation, methylation and triazole formation to deliver compounds of formula I wherein the R1 and/or R2 are selected as defined in formula I. Thioureas of formula XX are available from well established methods using for example an isothiocyanate R$^4$SCN (MeNCS shown in Scheme 5), or 1,1-thiocarbonyl-diimidazole in the presence of RNH$_2$, in a solvent such as methanol, ethanol and the like, at a temperature between room temperature and 100° C., and are typically carried out at 60° C. Alkylation of the thiourea intermediates can be performed using an alkylating agent such as iodomethane (shown in Scheme 5) or iodoethane, in a solvent such as DMF, acetone, CH$_2$Cl$_2$, at room temperature or elevated temperatures to give the isothiourea of formula XXI. When an iodoalkane is employed, the product may be isolated as the hydroiodide salt [see Synth. Commun. 1998, 28, 741-746]. Compounds of formula XXI may react with an acyl hydrazine or with hydrazine followed by an acylating agent to form an intermediate which may be cyclized to the 3-aminotriazoles of formula I by heating at 0 to 150° C. in a suitable solvent such as pyridine or DMF.

EXAMPLES

The invention will now be illustrated by the following non-limiting examples.

General Methods

All starting materials are commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.). Preparative reversed phase chromatography was run on a Gilson autopreparative HPLC with a diode array detector using an XTerra MS C8, 19×300 mm, 7 mm as column. Purification by a chromatotron was performed on rotating silica gel/gypsum (Merck, 60 PF-254 with calcium sulphate) coated glass sheets, with coating layer of 1, 2, or 4 mm using a TC Research 7924T chromatotron. Purification of products were also done by flash chromatography in silica-filled glass columns.

Microwave heating was performed in a Smith Synthesizer Single-mode microwave cavity producing continuous irradiation at 2450 MHz (Personal Chemistry AB, Uppsala, Sweden).

Example 1.1

(R)-Piperidine-1,2-dicarboxylic acid 1-tert-butyl ester 2-methyl ester

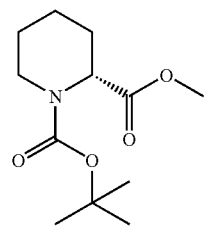

To (R)-Piperidine-1,2-dicarboxylic acid 1-tert-butyl ester (5.1 g, 22.2 mmol) in DMF (60 mL) were added K$_2$CO$_3$ (12.3 g, 88.8 mmol) and MeI (1.7 mL, 26.6 mmol). After stirring at room temperature overnight, the reaction mixture was diluted with ethyl acetate. The organic layer washed with water (6 times) and brine, dried over anhydrous Na$_2$SO$_4$, filtered and concentrated to give the title product (5.4 g, 99%).

$^1$H NMR (300 MHz, CDCl$_3$): δ (ppm) 4.82 (m, 1H), 3.99 (m, 1H), 3.75 (s, 3H), 2.95 (m, 1H), 2.21 (m, 1H), 2.45 (m, 14H)

In a similar manner the following compounds were synthesized:

| | | | |
|---|---|---|---|
| 1.2 | 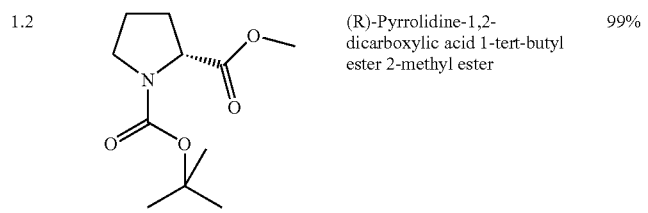 | (R)-Pyrrolidine-1,2-dicarboxylic acid 1-tert-butyl ester 2-methyl ester | 99% |

¹H NMR (300 MHz, CDCl₃): δ (ppm) 4.20-4.25 (m, 1H), 3.73-3.74 (m, 3H), 3.46-3.55 (m, 2H), 2.18-2.24 (m, 1H), 1.86-1.99 (m, 3H), 1.42-1.47 (m, 9H)

| | | | |
|---|---|---|---|
| 1.3 | 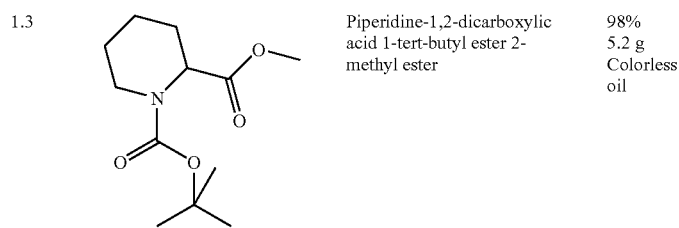 | Piperidine-1,2-dicarboxylic acid 1-tert-butyl ester 2-methyl ester | 98% 5.2 g Colorless oil |

¹H NMR (300 MHz, CDCl₃): δ (ppm) 4.82 (m, 1H), 3.99 (m, 1H), 3.75 (s, 3H), 2.95 (m, 1H), 2.21 (m, 1H), 2.45 (m, 14H)

Example 2.1

(R)-2-Formyl-piperidine-1-carboxylic acid tert-butyl ester

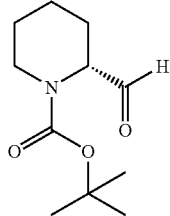

To the title compound of Example 1.1 (5.4 g, 22.1 mmol) in toluene (50 mL) at −78° C. was added 1.5 M DIBAL in toluene (33.8 mL, 50.7 mmol) drop-wise over 40 minutes. Methanol (120 mL) was then added drop-wise at −78° C. over 10 minutes. The reaction mixture was moved to an ice-bath where 10% wt citric acid (500 mL) was added and then mixture was stirred for an additional 1 hour. After the resulting mixture was extracted with ethyl acetate (2 times), the organic layer washed with water and brine, dried over anhydrous Na₂SO₄, filtered and concentrated to give the title product as a colorless oil (3.0 g, 64%).

¹H NMR (300 MHz, CDCl₃): δ (ppm) 9.61 (s, 1H), 4.60 (m, 1H), 4.96 (m, 1H), 2.91 (m, 1H), 2.19 (m, 1H), 1.49 (m, 14H)

In a similar manner the following compounds were synthesized:

| | | | |
|---|---|---|---|
| 2.2 | 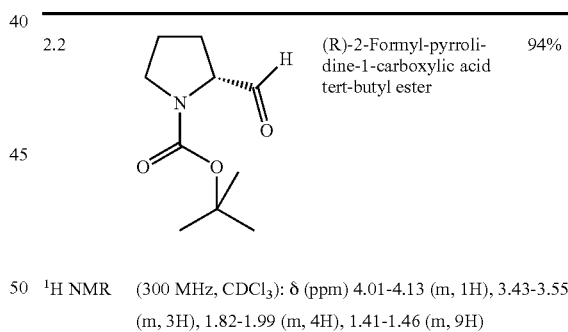 | (R)-2-Formyl-pyrrolidine-1-carboxylic acid tert-butyl ester | 94% |

¹H NMR (300 MHz, CDCl₃): δ (ppm) 4.01-4.13 (m, 1H), 3.43-3.55 (m, 3H), 1.82-1.99 (m, 4H), 1.41-1.46 (m, 9H)

| | | | |
|---|---|---|---|
| 2.3 | 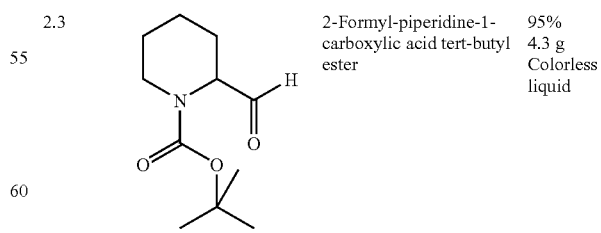 | 2-Formyl-piperidine-1-carboxylic acid tert-butyl ester | 95% 4.3 g Colorless liquid |

¹H NMR (300 MHz, CDCl₃): δ (ppm) 9.61 (s, 1H), 4.60 (m, 1H), 4.96 (m, 1H), 2.91 (m, 1H), 2.19 (m, 1H), 1.49 (m, 14H)

Example 3.1

(R)-2-(Hydroxyimino-methyl)-piperidine-1-carboxylic acid tert-butyl ester

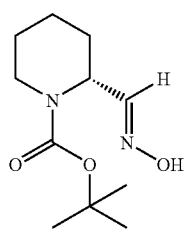

To the title compound of Example 2.1 (3.0 g, 14.1 mmol) in MeOH/H₂O (30 mL/30 mL) in an ice-bath was added Na₂CO₃ (895 mg, 8.4 mmol) and hydroxylamine hydrochloride (1.2 g, 16.9 mmol). After stirring for 30 minutes, the reaction mixture was warmed to room temperature and stirred for an additional 4 hours. The reaction mixture was concentrated to half volume and then extracted with ethyl acetate (2 times), washed with saturated brine, dried over anhydrous Na₂SO₄, filtered and concentrated to give the title product as a colorless oil (3.1 g, 97%).

$^1$H NMR (300 MHz, CDCl₃): δ (ppm) 7.40 (broad s, 1H), 7.40, 6.88 (d, 1H), 4.31 (m, 1H), 4.10 (m, 1H), 2.90 (m, 1H), 2.00 (m, 1H), 1.59 (m, 14H).

In a similar manner the following compounds were synthesized:

Example 4.1 tert-Butyl (2R)-2-[chloro(hydroxyimino)methyl]piperidine-1-carboxylate

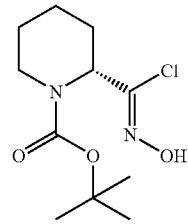

To the title compound of Example 3.1 (3.1 g, 13.7 mmol) in DMF (30 mL) at 40° C. was added N-chlorosuccinimide (2.0 g, 15.1 mmol) in 3 portions. After stirring for 1 hour, the reaction mixture was diluted with ethyl acetate and then the organic layer washed with water (3 times) and brine, dried over anhydrous Na₂SO₄, filtered and concentrated to give the title product (3.1 g, 85%).

$^1$H NMR (300 MHz, CDCl₃): δ (ppm) 8.79 (broad s, 1H), 4.31 (m, 1H), 3.99 (m, 1H), 2.90 (m, 1H), 2.28 (m, 1H), 1.59 (m, 14H).

In a similar manner the following compounds were synthesized:

| | | | |
|---|---|---|---|
| 3.2 | 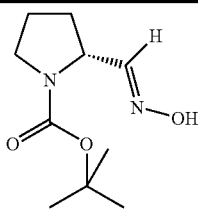 | (R)-2-(Hydroxyimino-methyl)-pyrrolidine-1-carboxylic acid tert-butyl ester | 99% |
| $^1$H NMR | (300 MHz, CDCl₃): δ (ppm) 8.11-8.19 (m, 1H), 7.15-7.23 (m, 1H), 4.09-4.16 (m, 1H), 3.41-3.45 (t, 2H), 1.84-2.02 (m, 4H), 1.45 (m, 9H) | | |
| 3.3 | 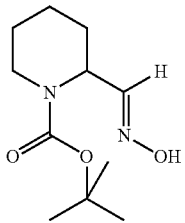 | 2-(Hydroxyimino-methyl)-piperidine-1-carboxylic acid tert-butyl ester | 100%<br>4.7 g |
| $^1$H NMR | (300 MHz, CDCl₃): δ (ppm) 7.40 (broad s, 1H), 6.88 (d, 1H), 4.31 (m, 1H), 4.10 (m, 1H), 2.90 (m, 1H), 2.00 (m, 1H), 1.59 (m, 14H) | | |

| | | | |
|---|---|---|---|
| 4.2 | (structure: tert-butyl (2R)-2-[(Z)-chloro(hydroxyimino)methyl]pyrrolidine-1-carboxylate) | tert-Butyl (2R)-2-[(Z)-chloro(hydroxyimino)-methyl]pyrrolidine-1-carboxylate | 84% |
| ¹H NMR | (300 MHz, CDCl₃): δ (ppm) 9.11-9.16 (m, 1H), 4.51-4.68 (m, 1H), 3.47-3.54 (m, 2H), 1.82-2.20 (m, 4H), 1.42-1.48 (m, 9H) | | |
| 4.3 | (structure: tert-butyl 2-[chloro(hydroxyimino)methyl]piperidine-1-carboxylate) | tert-Butyl-2-[chloro(hydroxyimino)methyl]piperidine-1-carboxylate | 93% 5.1 g |
| ¹H NMR | (300 MHz, CDCl₃): δ (ppm) 8.79 (broad s, 1H), 4.31 (m, 1H), 3.99 (m, 1H), 2.90 (m, 1H), 2.28 (m, 1H), 1.59 (m, 14H) | | |

The following compounds were synthesised according to the procedure in Example 18 in WO 2005/080386.

| | | | |
|---|---|---|---|
| 5.1 | (structure: 5-(3-chlorophenyl)isoxazol-3-yl piperidine Boc) | (R)-2-[5-(3-Chlorophenyl)-isoxazol-3-yl]-piperidine-1-carboxylic acid tert-butyl ester | 50% |
| ¹H NMR | (300 MHz, CDCl₃): δ (ppm) 7.75 (m, 1H), 7.65 (m, 1H), 7.41 (m, 2H), 5.51 (s br, 1H), 6.36 (s, 1H), 4.06 (m, 1H), 2.80 (m, 1H), 2.36 (m, 1H), 2.06 (m, 1H), 1.58-1.72 (m, 4H), 1.52 (s, 9H) | | |
| 5.2 | (structure: 5-(3-cyanophenyl)isoxazol-3-yl pyrrolidine Boc) | (R)-2-[5-(3-Cyanophenyl)-isoxazol-3-yl]-pyrrolidine-1-carboxylic acid tert-butyl ester | 78% |
| ¹H NMR | (300 MHz, CDcl₃): δ (ppm) 7.97-8.04 (m, 2H), 7.59-7.71 (m, 2H) 6.50-6.61 (m, 1H), 4.97-5.07 (m, 1H), 3.44-3.61 (m, 2H), 2.00-2.40 (m, 4H), 1.35-1.49 (m, 9H) | | |

| 5.3 | 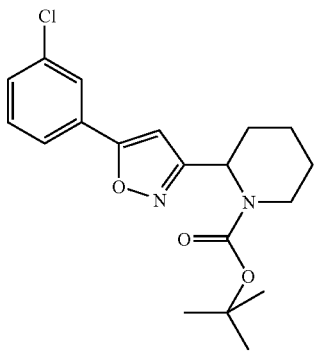 | 2-[5-(3-Chloro-phenyl)-isoxazol-3-yl]-piperidine-1-carboxylic acid tert-butyl ester | 70% |

¹H NMR (300 MHz, CDCl₃): δ (ppm) 7.75 (m, 1H), 7.65 (m, 1H), 7.41 (m, 2H), 6.36 (s, 1H), 5.51 (s br, 1H), 4.06 (m, 1H), 2.80 (m, 1H), 2.36 (m, 1H), 2.06 (m, 1H), 1.58-1.72 (m, 4H), 1.52 (s, 9H).

| 5.4 | 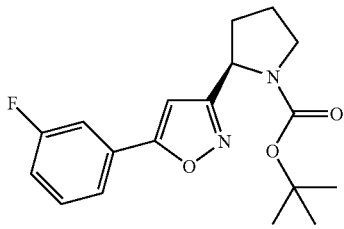 | (R)-2-[5-(3-Fluoro-phenyl)-isoxazol-3-yl]-pyrrolidine-1-carboxylic acid tert-butyl ester | 89% |

¹H NMR (500 MHz, CDCl₃): δ (ppm) 7.55-7.51 (m, 1H), 7.48-7.38 (m, 2H), 7.16-7.08 (m, 1H), 6.52 (s, 0.4H, minor rotamer), 6.40 (s, 0.6H, major rotamer), 5.11-4.93 (m, 1H), 3.70-3.40 (M, 2H), 2.44-1.82 (m, 4H), 1.52-1.32 (m, 9H)

| 5.5 | 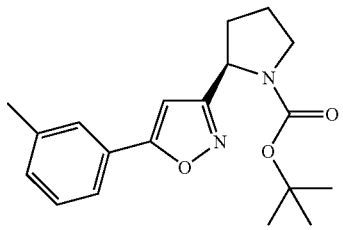 | (R)-2-(5-m-Tolyl-isoxazol-3-yl)-pyrrolidine-1-carboxylic acid tert-butyl ester | 58% |

¹H NMR (400 MHz, CDCl₃: δ (ppm) 7.55 (m, 2H), 7.34 (m, 1H), 7.23 (m, 1H), 6.47 (broad s, 0.4 H, minor rotamer), 6.36 (broad s, 0.6 H, major rotamer), 5.07 (m, 0.4H, minor rotamer), 4.97 (m, 0.6H, major rotamer), 3.65-3.38 (m, 2H), 2.41 (s, 3H), 2.38-1.91 (m, 4H), 1.48 (s, 3.6H, minor rotamer), 1.34 (s, 5.4H, major rotamer)

| 5.6 | 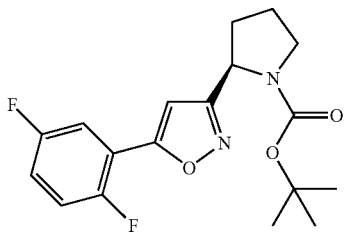 | (R)-2-[5-(2,5-Difluoro-phenyl)-isoxazol-3-yl]-pyrrolidine-1-carboxylic acid tert-butyl ester | 75% |

¹H NMR (500 MHz, CDCl₃): δ 7.61 (m, 1H), 7.11 (m, 2H), 6.63 (m, 1H), 4.92-5.10 (m, 1H), 3.42-3.58 (m, 2H), 2.08-2.36 (m, 2H), 1.98 (m, 2H), 1.32-1.48 (m, 9H)

| | | | |
|---|---|---|---|
| 5.7 | 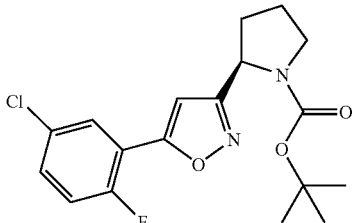 | (R)-2-[5-(5-Chloro-2-fluoro-phenyl)-isoxazol-3-yl]-pyrrolidine-1-carboxylic acid tert-butyl ester | 87% |
| $^1$H NMR | (500 MHz, CDCl$_3$): δ (ppm) 7.92 (m, 1H), 7.36 (m, 1H), 7.14 (m, 1H), 6.64 (m, 1H), 5.06 (m, 1H), 3.49 (m, 2H), 1.83-2.38 (m, 4H), 1.40-1.52 (m, 9H) | | |
| 5.8 | 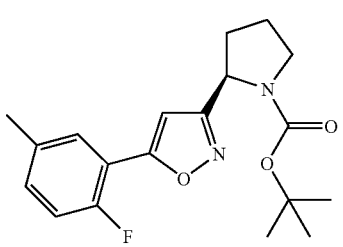 | (R)-2-[5-(2-Fluoro-5-methyl-phenyl)-isoxazol-3-yl]-pyrrolidine-1-carboxylic acid tert-butyl ester | 68% |
| $^1$H NMR | (500 MHz, CDCl$_3$): δ (ppm) 7.71 (m, 1H), 7.17 (m, 1H), 7.03 (m, 1H), 6.57 (m, 1H), 5.03 (m, 1H), 3.50 (m, 2H), 1.90-2.39 (m, 7H), 1.32-1.50 (m, 9H) | | |

The following compounds were synthesised according to the procedure in Example 23 in WO 2005/080386.

| | | | |
|---|---|---|---|
| 6.1 | 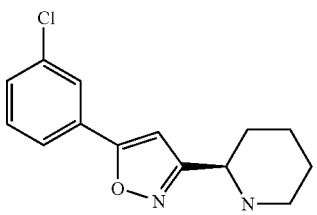 | (R)-2-[5-(3-Chloro-phenyl)-isoxazol-3-yl]-piperidine | 93% |
| $^1$H NMR | (300 MHz, CDCl$_3$): δ (ppm) 8.03 (s, 1H), 7.75 (m, 1H), 7.64 (m, 1H), 7.40 (m, 2H), 6.60 (s, 1H), 3.93 (d of d, 1H), 3.18 (m, 1H), 2.82 (t of d, 1H), 1.53-1.93 (m, 6H) | | |
| 6.2 | 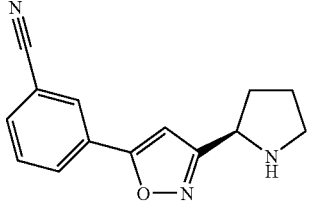 | 3-((R)-3-Pyrrolidin-2-yl-isoxazol-5-yl)-benzonitrile | 100% |
| $^1$H NMR | (300 MHz, CDCl$_3$): δ (ppm) 8.02 (s, 1H), 7.97 (dd, 1H), 7.69 (dd, 1H), 7.58 (t, 1H), 6.62 (s, 1H), 4.34-4.39 (t, 1H), 3.04-3.15 (m, 2H), 2.20-2.30 (m, 2H), 1.85-1.94 (m, 3H) | | |
| 6.3 | 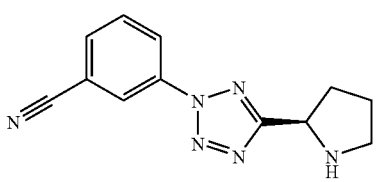 | 3-((R)-5-Pyrrolidin-2-yl-tetrazol-2-yl)-benzonitrile | 97% |

| | | | |
|---|---|---|---|
| ¹H NMR | (300 MHz, CDCl₃): δ (ppm) 8.47 (t, 1H), 8.43 (dd, 1H), 7.78 (dd, 1H), 7.13 (t, 1H), 4.66 (q, 1H), 3.23-3.25 (m, 1H), 3.12-3.21 (m, 1H), 2.20-2.42 (m, 2H), 2.12-2.19 (m, 2H), 1.96-2.04 (m, 2H) | | |
| 6.4 | 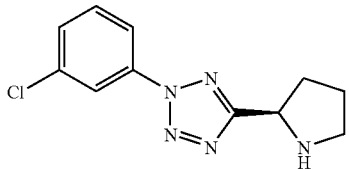 | 2-(3-Chloro-phenyl)-5-(R)-pyrrolidin-2-yl-2H-tetrazole | 98% |
| ¹H NMR | (300 MHz, CDCl₃): δ (ppm) 8.15 (dd, 1H), 8.02 (dt, 1H), 7.46-7.51 (m, 2H), 4.65 (t, 1H), 3.21-3.26 (m, 2H), 3.11-3.16 (m, 1H), 2.33-2.35 (m, 1H), 2.14-2.19 (m, 1H), 1.97-2.03 (m, 2H) | | |
| 6.5 | 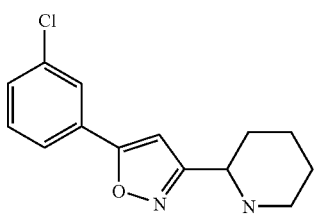 | 2-[5-(3-Chloro-phenyl)-isoxazol-3-yl]-piperidine | 88% |
| ¹H NMR | (300 MHz, CDCl₃): δ (ppm) 8.03 (s, 1H), 7.75 (m, 1H), 7.64 (m, 1H), 7.40 (m, 2H), 6.60 (s, 1H), 3.93 (d of d, 1H), 3.18 (m, 1H), 2.82 (t of d, 1H), 1.53-1.93 (m, 6H) | | |
| 6.6 | 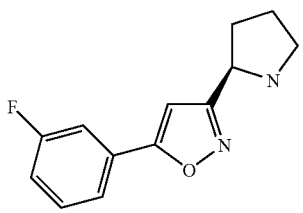 | 5-(3-Fluoro-phenyl)-3-(R)-pyrrolidin-2-yl-isoxazole | 91% |
| ¹H NMR | (500 MHz, CDCl3): δ (ppm) 7.55-7.51 (m, 1H), 7.47-7.39 (m, 2H), 7.14-7.09 (m, 1H), 6.57 (s, 1H), 4.44-4.39 (m, 1H), 3.61-3.40 (m, 1H), 3.22-3.16 (m, 1H), 3.13-3.07 (m, 1H), 2.32-2.22 (m, 1H), 2..01-1.87 (m, 3H) | | |
| 6.7 | 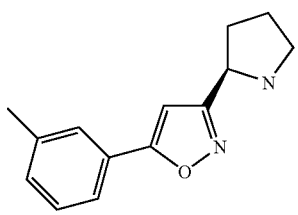 | 3-(R)-Pyrrolidin-2-yl-5-m-tolyl-isoxazole | 93% |
| ¹H NMR | (400 MHz, CDCl₃): δ (ppm) 7.58 (broad s, 1H), 7.55 (d, 1H), 7.32 (t, 1H), 7.22 (d, 1H), 6.49 (s, 1H), 4.34 (dd, 1H), 3.16 (m, 1H), 3.04 (m, 1H), 2.40 (s, 3H), 2.23 (m, 1H), 2.12 (broad s, 1H), 1.91 (m, 3H). | | |
| 6.7 | 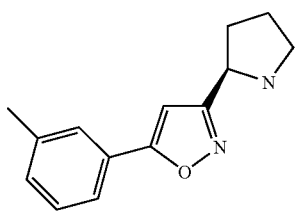 | 3-(R)-Pyrrolidin-2-yl-5-m-tolyl-isoxazole | 93% |
| ¹H NMR | (400 MHz, CDCl₃): δ (ppm) 7.58 (broad s, 1H), 7.55 (d, 1H), 7.32 (t, 1H), 7.22 (d, 1H), 6.49 (s, 1H), 4.34 (dd, 1H), 3.16 (m, 1H), 3.04 (m, 1H), 2.40 (s, 3H), 2.23 (m, 1H), 2.12 (broad s, 1H), 1.91 (m, 3H). | | |

-continued

| | | | |
|---|---|---|---|
| 6.8 | [structure: 5-(2,5-difluorophenyl)-3-(R)-pyrrolidin-2-yl-isoxazole] | 5-(2,5-Difluoro-phenyl)-3-(R)-pyrrolidin-2-yl-isoxazole | 87% |
| ¹H NMR | (500 MHz, CDCl₃): δ (ppm) 7.61 (m, 1H), 7.11 (m, 2H), 6.63 (m, 1H), 4.92-5.10 (m, 1H), 3.42-3.58 (m, 2H), 2.08-2.36 (m, 2H), 1.98 (m, 2H), 1.32-1.48 (m, 9H) | | |
| 6.9 | [structure] | 5-(5-Chloro-2-fluoro-phenyl)-3-(R)-pyrrolidin-2-yl-isoxazole | 87% |
| ¹H NMR | (500 MHz, CDCl₃): δ 7.87 (m, 1H), 7.34 (m, 1H), 7.11 (m, 1H), 6.79 (m, 1H), 4.52 (m, 1H), 3.14-3.28 (m, 2H), 2.25-2.40 (m, 2H), 1.99 (m, 2H) | | |
| 6.10 | [structure] | 5-(2-Fluoro-5-methyl-phenyl)-3-(R)-pyrrolidin-2-yl-isoxazole | 99% |
| ¹H NMR | (500 MHz, CDCl₃): δ (ppm) 7.63 (m, 1H), 7.19 (m, 1H), 7.03 (m, 1H), 6.81 (m, 1H), 4.97 (m, 1H), 3.57 (m, 2H), 2.52 (m, 1H), 2.15-2.38 (m, 6H) | | |

The following compounds were synthesised according to the procedure in Example 73 in WO 2005/080386.

| | | | |
|---|---|---|---|
| 7.1 | [structure] | (R)-2-[5-(3-Chloro-phenyl)-isoxazol-3-yl]-piperidine-1-carbothioic acid methylamide | 100% |
| ¹H NMR | (300 MHz, CDCl₃): δ (ppm) 7.73 (s, 1H), 7.63 (m, 1H), 7.39 (m, 2H), 6.78 (d, 1H), 6.50 (s, 1H), 5.94 (d, 1H), 4.06 (d, 1H), 3.21 (d, 3H), 3.14 (m, 1H), 2.35 (d, 1H), 1.72-1.98 (m, 5H) | | |

| | | | |
|---|---|---|---|
| 7.2 | 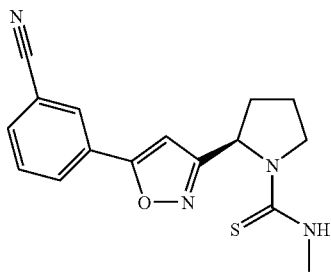 | (R)-2-[5-(3-Cyano-phenyl)-isoxazol-3-yl]-pyrrolidine-1-carbothioic acid methylamide | 72% |
| ¹H NMR | (300 MHz, CDCl₃): δ 8.05 (s, 1H), 7.98 (dd, 1H), 7.73 (dd, 1H), 7.62 (t, 1H), 6.70 (s, 1H), 5.66-5.76 (m, 2H), 3.73-3.81 (m, 2H), 3.13 (d, 3H), 2.19-2.42 (m, 4H) | | |
| 7.3 | 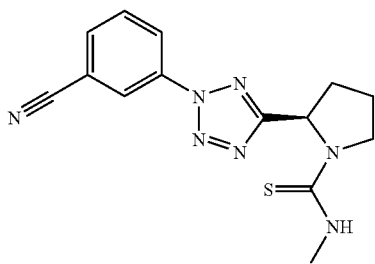 | (R)-2-[2-(3-Cyano-phenyl)-2H-tetrazol-5-yl]-pyrrolidine-1-carbothioic acid methylamide | 94% |
| ¹H NMR | (300 MHz, CDCl₃): δ (ppm) 8.39-8.44 (m, 2H), 7.78 (dd, 1H), 7.72 (t, 1H), 5.89-5.99 (m, 2H), 3.68-3.77 (m, 1H), 3.46-3.53 (m, 1H), 3.15 (d, 3H), 2.38-2.45 (m, 2H), 2.24-2.26 (m, 2H) | | |
| 7.4 | 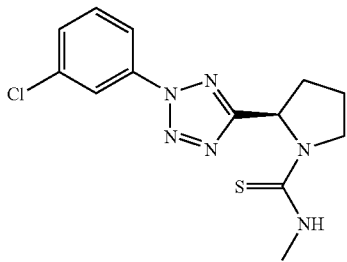 | (R)-2-[2-(3-Chloro-phenyl)-2H-tetrazol-5-yl]-pyrrolidine-1-carbothioic acid methylamide | 68% |
| ¹H NMR | (300 MHz, CDCl₃): δ (ppm) 8.13-8.15 (m, 2H), 8.02-8.06 (m, 1H), 7.47-7.51 (m, 2H), 5.75-5.99 (m, 2H), 3.90 (t, 1H), 3.76 (q, 1H), 3.16 (d, 3H), 2.19-2.49 (m, 4H) | | |
| 7.5 | 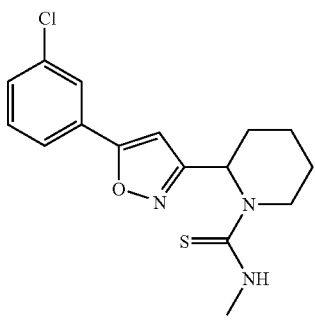 | 2-[5-(3-Chloro-phenyl)-isoxazol-3-yl]-piperidine-1-carbothioic acid methylamide | 79% |
| ¹H NMR | Identical to Example 7.1 | | |

| | | | |
|---|---|---|---|
| 7.6 | | (R)-2-[5-(3-Fluoro-phenyl)-isoxazol-3-yl]-pyrrolidine-1-carbothioic acid methylamide | 73% |
| ¹H NMR | (500 MHz, CDCl₃): δ (ppm) 7.55-7.51 (m, 1H) 7.47-7.40 (m, 2H), 7.16-7.10 (m, 1H), 6.56 (s, 1H), 5.74 (s, broad, 1H), 5.52 (s, broad, 1H), 3.92-3.70 (m, 2H), 3.11 (d, 3H), 2.44-2.33 (m, 1H), 2.30-2.11 (m, 3H) | | |
| 7.7 | | (R)-2-(5-m-Tolyl-isoxazol-3-yl)-pyrrolidine-1-carbothioic acid methylamide | 73% |
| ¹H NMR | (400 MHz, CDCl₃): δ (ppm) 7.56 (m, 2H), 7.34 (t, 1H), 7.25 (m, 1H), 6.49 (s, 1H), 5.79 (broad s, 1H), 5.40 (broad s, 1H), 3.88 (m, 2H), 3.10 (d, 3H), 2.40 (m, 4H), 2.30-2.10 (m, 3H) | | |
| 7.8 | | (R)-2-[5-(2,5-Difluoro-phenyl)-isoxazol-3-yl]-pyrrolidine-1-carbothioic acid methylamide | 79% |
| ¹H NMR | (500 MHz, CDCl₃): δ 7.58 (m, 1H), 7.12 (m, 2H), 6.71 (m, 1H), 5.54 (bs, 1H), 3.85 (m, 2H), 3.11 (s, 3H), 2.40 (m, 1H), 2.13-2.25 (m, 3H) | | |
| 7.9 | | (R)-2-[5-(5-Chloro-2-fluoro-phenyl)-isoxazol-3-yl]-pyrrolidine-1-carbothioic acid methylamide | 85% |
| ¹H NMR | (500 MHz, CDCl₃): δ (ppm) 7.87 (m, 1H), 7.36 (m, 1H), 7.13 (m, 1H), 6.68 (d, 1H), 5.71 (bs, 1H), 5.50 (bs, 1H), 3.80 (m, 2H), 3.09 (d, 3H), 2.39 (m, 1H), 2.19 (m, 3H) | | |
| 7.10 | | (R)-2-[5-(2-Fluoro-5-methyl-phenyl)-isoxazol-3-yl]-pyrrolidine-1-carbothioic acid methylamide | 67% |
| ¹H NMR | (500 MHz, CDCl₃): δ (ppm) 7.68 (m, 1H), 7.19 (m, 1H), 7.05 (m, 1H), 6.62 (m, 1H), 5.43 (bs, 1H), 3.89 (bs, 2H), 3.09 (s, 3H), 2.42 (m, 1H), 2.35 (s, 3H), 2.10-2.25 (m, 3H) | | |

Example 8.1

(R)-2-[5-(3-Chloro-phenyl)-isoxazol-3-yl]-N-methyl-piperidine-1-carboximidothioic acid methyl ester

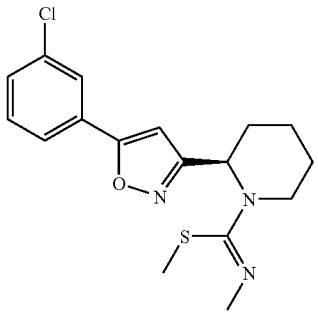

To the title compound of Example 7.1 (153 mg, 0.47 mmol) in THF (2 mL) at room temperature were added sodium tert-butoxide (45 mg, 0.47 mmol) and $CH_3I$ (0.044 mL, 0.70 mmol). After stirring the reaction mixture for 1 hour, the reaction mixture was diluted with water and then extracted with ethyl acetate. The organic layer washed with water and brine, dried over anhydrous $Na_2SO_4$, filtered and concentrated to give the title product as a light yellow solid (150 mg, 94%).

$^1$H NMR (300 MHz, $CDCl_3$): δ (ppm) 8.04 (s, 1H), 8.00 (d, 1H), 7.92 (d, 1H), 7.60 (t, 1H), 6.51 (s, 1H), 5.46 (m, 1H), 3.86 (m, 1H), 3.27 (s, 3H), 3.04 (m, 1H), 2.36 (m, 4H), 1.96 (m, 1H), 1.76 (m, 2H), 1.66 (m, 2H).

In a similar manner the following compounds were synthesized:

| 8.2 | 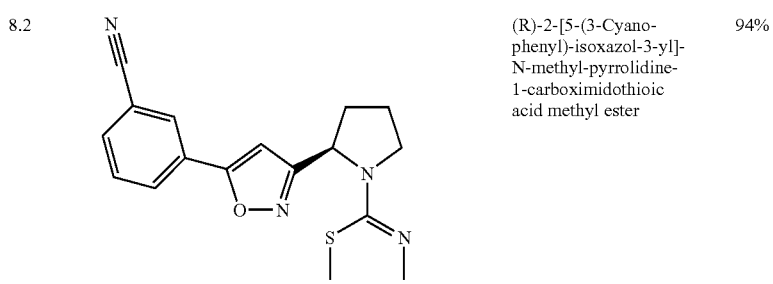 | (R)-2-[5-(3-Cyano-phenyl)-isoxazol-3-yl]-N-methyl-pyrrolidine-1-carboximidothioic acid methyl ester | 94% |
|---|---|---|---|

$^1$H NMR  (300 MHz, $CDCl_3$): δ (ppm) 8.05 (s, 1H), 7.99 (dd, 1H), 7.71 (dd, 1H), 7.63 (t, 1H), 6.48 (s, 1H), 5.38-5.41 (m, 1H), 3.60-3.77 (m, 2H), 3.25 (s, 2H), 2.30-2.41 (m, 4H), 2.00-2.10 (m, 3H)

| 8.3 | 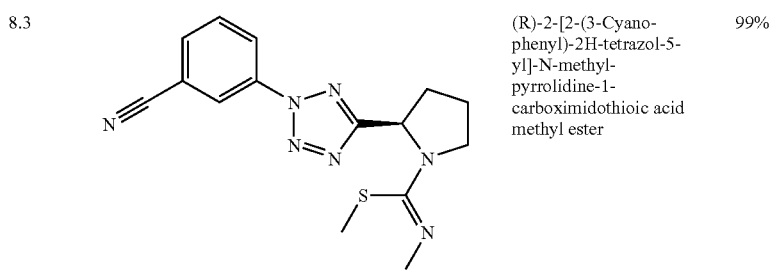 | (R)-2-[2-(3-Cyano-phenyl)-2H-tetrazol-5-yl]-N-methyl-pyrrolidine-1-carboximidothioic acid methyl ester | 99% |
|---|---|---|---|

$^1$H NMR  (300 MHz, $CDCl_3$): δ (ppm) 8.39-8.43 (m, 2H), 7.76 (dd, 1H), 7.70 (t, 1H), 5.59-5.63 (m, 1H), 3.83-3.85 (m, 1H), 3.68-3.71 (m, 1H), 2.40-2.51 (m, 1H), 2.27 (s, 3H), 2.06-2.17 (m, 3H)

| 8.4 | 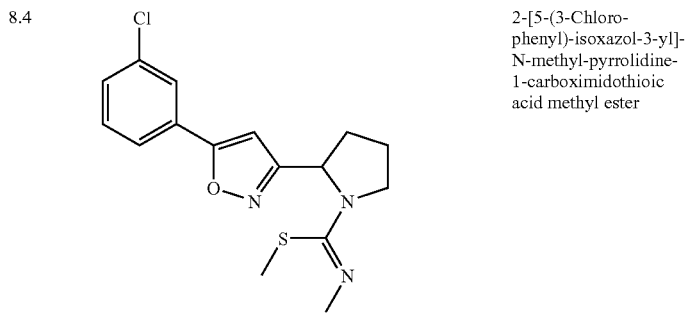 | 2-[5-(3-Chloro-phenyl)-isoxazol-3-yl]-N-methyl-pyrrolidine-1-carboximidothioic acid methyl ester | Previously described in Example 75 in WO 2005/080386. |
|---|---|---|---|

-continued

| | | | |
|---|---|---|---|
| 8.5 | 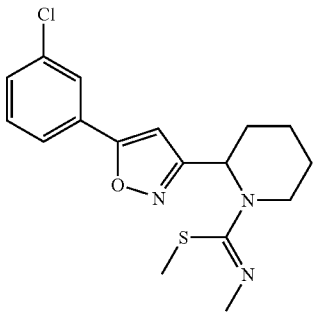 | 2-[5-(3-Chloro-phenyl)-isoxazol-3-yl]-piperidine-1-carbothioic acid methylamide | Previously described in Example 75 in WO 2005/080386 99% |
| 8.6 | 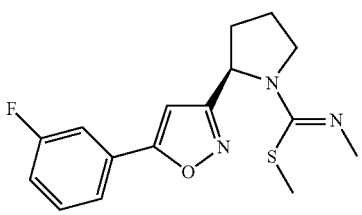 | (R)-2-[5-(3-Fluoro-phenyl)-isoxazol-3-yl]-N-methyl-pyrrolidine-1-carboximidothioic acid methyl ester | 99% |
| $^1$H NMR | (500 MHz, CDCl$_3$): δ (ppm) 7.55-7.52 (m, 1H), 7.47-7.39 (m, 2H), 7.14-7.09 (m, 1H), 6.36 (s, 1H), 5.41-5.36 (m, 1H), 3.76-3.69 (m, 1H), 3.67-3.59 (m, 1H), 3.24 (s, 3H), 2.41-2.30 (m, 1H), 2.26 (s, 3H), 2.17-2.10 (m, 1H), 2.07-1.95 (m, 2H) | | |
| 8.7 | 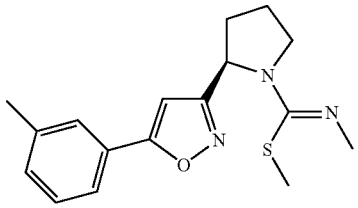 | (R)-N-Methyl-2-(5-m-tolyl-isoxazol-3-yl)-pyrrolidine-1-carboximidothioic acid methyl ester | Quantitative |
| $^1$H NMR | (400 MHz, CDCl$_3$): δ (ppm) 7.55 (m, 2H), 7.33 (t, 1H), 7.22 (d, 1H), 6.34 (s, 1H), 5.39 (dd, 1H), 3.72 (m, 1H), 3.62 (m, 1H), 3.24 (s, 3H), 2.40 (s, 3H), 2.34 (m, 1H), 2.24 (s, 3H), 2.12 (m, 1H), 2.00 (m, 2H) | | |
| 8.8 | 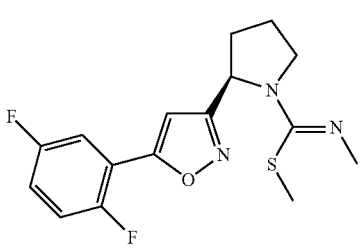 | (R)-2-[5-(2,5-Difluoro-phenyl)-isoxazol-3-yl]-N-methyl-pyrrolidine-1-carboximidothioic acid methyl ester | 96% |
| $^1$H NMR | (500 MHz, CDCl$_3$): δ (ppm) 7.59 (m, 1H), 7.10 (m, 2H), 6.58 (m, 1H), 5.43 (br, 1H), 3.61-3.78 (m, 2H), 3.21 (s, 3H), 2.29-2.39 (m, 1H), 2.27 (s, 3H), 2.09 (m, 1H), 2.00 (m, 2H) | | |
| 8.9 | 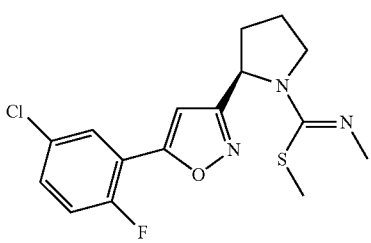 | (R)-2-[5-(5-Chloro-2-fluoro-phenyl)-isoxazol-3-yl]-N-methyl-pyrrolidine-1-carboximidothioic acid methyl ester | 99% |
| $^1$H NMR | (500 MHz, CDCl$_3$): δ (ppm) 7.88 (m, 1H), 7.33 (m, 1H), 7.10 (m, 1H), 6.55 (m, 1H), 5.39 (bs, 1H), 3.68 (m, 2H), 3.20 (s, 3H), 3.14 (m, 1H), 2.25 (s, 3H), 2.10, (m, 1H), 1.99 (m, 2H) | | |

| | | | |
|---|---|---|---|
| 8.10 | 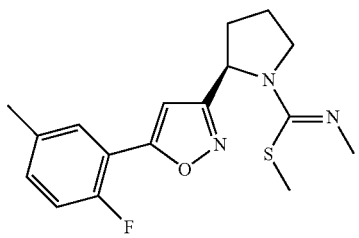 | (R)-2-[5-(2-Fluoro-5-methyl-phenyl)-isoxazol-3-yl]-N-methyl-pyrrolidine-1-carboximidothioic acid methyl ester | 99% |

$^1$H NMR (500 MHz, CDCl$_3$): δ (ppm) 7.69 (m, 1H), 7.16 (m, 1H), 7.03 (m, 1H), 6.53 (m, 1H), 5.47 (bs, 1H), 3.72 (m, 2H), 3.23 (s, 3H), 2.36 (s, 3H), 2.28 (s, 3H), 1.97-2.14 (m, 3H), 1.83 (m, 1H)

Example 9

(R)-2-[2-(3-Chloro-phenyl)-2H-tetrazol-5-yl]-N-methyl-pyrrolidine-1-carboximidothioic acid methyl ester

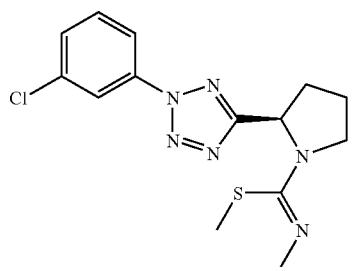

Title compound of Example 7.4 (0.385 g, 1.20 mmol) and methyl iodide (0.30 g, 2.1 mmol) in MeOH (5.0 mL) were stirred at 80° C. for 1 h. The reaction was concentrated and partitioned with CH$_2$Cl$_2$ and sodium carbonate. The organic extracts were washed with brine, dried over sodium sulphate, filtered and concentrated to afford the title product (0.40 g, 88%) as an amber oil.

$^1$H NMR (300 MHz, CDCl$_3$): δ (ppm) 8.15 (t, 1H), 8.03 (dt, 1H), 7.43-7.51 (m, 2H), 5.60-5.63 (m, 1H), 3.82-3.84 (m, 1H), 3.67-3.70 (m, 1H), 3.19 (s, 3H), 2.40-2.43 (m, 1H), 2.27 (s, 3H), 2.02-2.17 (m, 3H).

Example 10

(R)-2-Carbamoyl-pyrrolidine-1-carboxylic acid tert-butyl ester

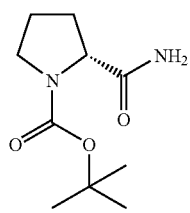

N-Methylmorpholine (9.85 g, 97.5 mmol) and isobutyl chloroformate (13.33 g, 97.5 mmol) was added to (R)-pyrrolidine-1,2-dicarboxylic acid 1-tert-butyl ester (20.0 g, 92.9 mmol) in THF (200 mL) at −78° C. and stirred for 1 h. Ammonium hydroxide (58 mL) was added slowly as the reaction warmed up to RT and stirred for a further 2 h. The reaction mixture was partitioned between DCM and water. The organic extracts were washed with 1 M HCl, dried over sodium sulphate, filtered and concentrated to afford the title product (10.8 g, 54%) as a colourless semisolid.

$^1$H NMR (300 MHz, CDCl$_3$): δ (ppm) 5.91-6.13 (m, 1H), 4.17-4.30 (m, 2H), 3.37-3.48 (m, 2H), 2.10-2.18 (m, 2H), 1.84-1.96 (m, 2H), 1.45 (s, 9H).

Example 11

(R)-2-Cyano-pyrrolidine-1-carboxylic acid tert-butyl ester

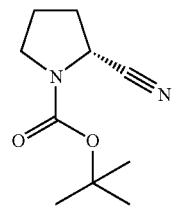

The title product of Example 10 (10.81 g, 50.45 mmol) and cyanuric chloride (5.58 g, 30.3 mmol) was stirred in DMF (30 mL) for 1 h. The reaction mixture was partitioned between ethyl acetate and water. The organic extracts were washed with aq. sodium carbonate, water, brine dried over sodium sulphate, filtered and concentrated to afford the title product (8.34 g, 84%) as a colourless oil.

$^1$H NMR (300 MHz, CDCl$_3$): δ (ppm) 4.42-4.55 (m, 1H), 3.32-3.52 (m, 2H), 2.00-2.27 (m, 4H), 1.46-1.50 (m, 9H).

Example 12

(R)-2-(2H-Tetrazol-5-yl)-pyrrolidine-1-carboxylic acid tert-butyl ester

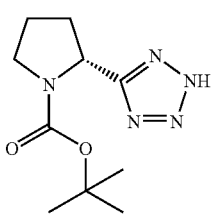

The title compound of Example 11 (8.34 g, 42.5 mmol), sodium azide (3.04 g, 46.8 mmol), and ammonium chloride (2.50 g, 46.8 mmol) were stirred in DMF (30 mL) at 100° C. for 12 h. The reaction was concentrate and partitioned with DCM and 3 M HCl. The organic extracts were dried over sodium sulphate, filtered and concentrated. The resulting solid was triturated with ether and filtered to afford the title product (5.31 g, 52%) as a white solid.

$^1$H NMR (300 MHz, CDCl$_3$): δ (ppm) 5.09-5.12 (m, 2H), 3.43-3.65 (m, 2H), 2.81-2.95 (m, 1H), 2.04-2.18 (m, 4H), 1.29-1.49 (m, 9H).

Example 13.1

(R)-2-[2-(3-Bromo-phenyl)-2H-tetrazol-5-yl]-pyrrolidine-1-carboxylic acid tert-butyl ester

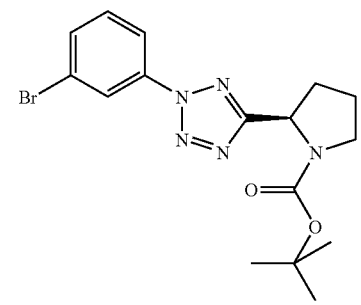

The title compound of Example 12 (4.88 g, 20.4 mmol), title compound of Example 16.2 (11.8 g, 22.4 mmol), sodium tert-butoxide (2.15 g, 22.4 mmol), BINAP (0.508 g, 0.816 mmol), Pd$_2$(dba)$_3$ (0.211 g, 0.204 mmol), copper 2-phenylpropane carboxylate (0.157 g, 0.408 mmol) in t-BuOH (150 mL) was stirred at 90° C. for 12 h. The reaction mixture was concentrated on silica gel and purified by column chromatography to afford the title product (4.97 g, 62%) as a yellow oil.

$^1$H NMR (300 MHz, CDCl$_3$): δ (ppm) 8.31 (s, 1H), 8.08 (d, 1H), 7.62 (t, 1H), 7.44 (q, 1H), 5.22-5.34 (m, 1H), 3.73-3.75 (m, 1H), 3.54-3.61 (m, 1H), 2.37-2.43 (m, 1H), 1.98-2.16 (m, 3H), 1.42 (s, 3H), 1.27 (s, 6H).

In a similar manner the following compound were synthesized:

Example 14

(R)-2-[2-(3-Cyano-phenyl)-2H-tetrazol-5-yl]-pyrrolidine-1-carboxylic acid tert-butyl ester

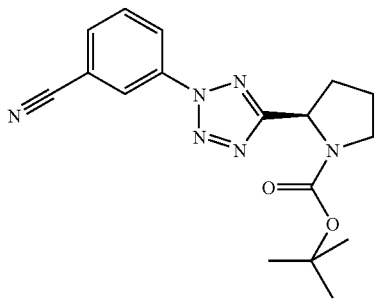

The title compound of Example 13.1 (4.97 g, 12.61 mmol), dppf (0.042 g, 0.076 mmol), zinc cyanide (0.89, 7.57 mmol), Pd$_2$(dba)$_3$ (0.026 g, 0.025 mmol), zinc acetate (0.185 g, 1.01 mmol) and Zn dust (0.066 g, 1.01 mmol) were stirred in DMF (50 mL) and water (1.5 mL) for 12 h at 90° C. and a further 6 h at 120° C. The reaction mixture was partitioned between ethyl acetate and water. The organic extracts were dried over sodium sulphate, filtered and concentrated and purified by column chromatography to afford the title product (1.83 g, 43%).

$^1$H NMR (300 MHz, CDCl$_3$): δ (ppm) 8.39-8.44 (m, 2H), 7.66-7.81 (m, 2H), 5.22-5.35 (m, 1H), 3.73-3.76 (m, 1H), 3.54-3.72 (m, 1H), 2.37-2.45 (m, 1H), 2.00-2.18 (m, 3H), 1.42 (s, 3H), 1.27 (s, 6H).

Example 15.1 m-Chlorophenyliodine diacetate

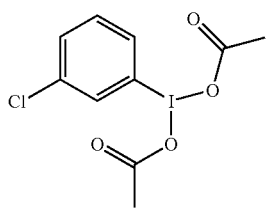

1-Chloro-3-iodobenzene (5.0 g, 21 mmol) was stirred at 30° C. Peracetic acid (40%, 8.35 mL, 50.3 mmol) was added drop wise to the solution and the reaction was allowed to stir for 12 h. The white solid that formed was filtered, washed 1

| | | | |
|---|---|---|---|
| 13.2 | 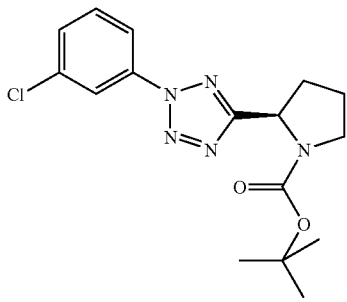 | (R)-2-[2-(3-Chlorophenyl)-2H-tetrazol-5-yl]-pyrrolidine-1-carboxylic acid tert-butyl ester | 58% |

$^1$H NMR (300 MHz, CDCl$_3$): δ (ppm) 8.74 (s, 1H), 8.15 (d, 1H), 7.41-7.48 (m, 2H), 5.21-5.34 (m, 1H), 3.72-3.74 (m, 1H), 3.50-3.60 (m, 1H), 2.33-2.50 m, 1H), 1.98-2.18 (m, 3H), 1.28-1.46 (m, 9H)

time with 10% acetic acid, and 3 times with hexanes and dried in vacuo to afford the title product (27.5 g, 92%) as a white solid.

$^1$H NMR (300 MHz, CDCl$_3$): δ (ppm) 8.10 (s, 1H), 7.99 (d, 1H), 7.57 (d, 1H), 7.46 (t, 1H), 2.04 (s, 6H).

In a similar manner the following compounds were synthesized:

| 15.2 | 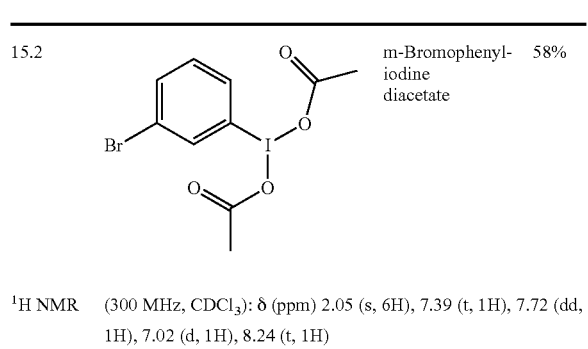 | m-Bromophenyl-iodine diacetate | 58% |
|---|---|---|---|
| $^1$H NMR | (300 MHz, CDCl$_3$): δ (ppm) 2.05 (s, 6H), 7.39 (t, 1H), 7.72 (dd, 1H), 7.02 (d, 1H), 8.24 (t, 1H) | | |

Example 16.1

Bis(3-chlorophenyl)iodonium tetrafluoroborate

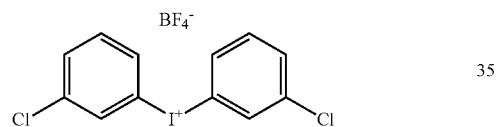

Borontrifluoride diethyl etherate (16.51 g, 116.3 mmol) was added slowly to 3-chlorophenyl boronic acid (17.37 g, 111.0 mmol) in DCM (170 mL) at −5° C., while stirring. After 15 minutes, the title compound of Example 15.1 (37.71 g, 105.8 mmol) in DCM (150 mL) was added slowly. The reaction stirred for 1 h at 0° C. and sodium tetrafluoroborate (225 g in 300 mL water) was added and stirred for 1 h. The organic layer was separated, dried over sodium sulphate, filtered and concentrated and triturated with ether to afford the title product (31.6 g, 68%) as a light brown solid.

$^1$H NMR (300 MHz, (CD$_3$)$_2$SO): δ (ppm) 7.60 (t, 2H), 7.74 (dd, 2H), 8.26 (dd, 2H), 8.50 (s, 2H).

In a similar manner the following compound was synthesized:

Example 17

3-Trimethylsilanylethynyl-benzonitrile

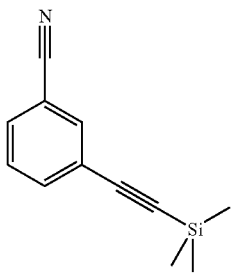

3-Iodo-benzonitrile (10.0 g, 43.7 mmol), trilmethylsilane acetylene (5.57 g, 56.8 mmol), palladium tetrakis triphenylphosphine (2.02 g, 1.75 mmol), and copper iodide (1.0 g, 5.24 mmol) in triethylamine (120 mL) was stirred for 12 h. The reaction was concentrated and purified by column chromatography to afford the title product (9.35 g, quantitative yield) as a brown oil.

$^1$H NMR (300 MHz, CDCl$_3$): δ (ppm) 7.76 (t, 1H), 7.71 (dd, 1H), 7.63 (dd, 1H), 7.28 (t, 1H), 0.26 (s, 9H).

Example 18

3-Ethynyl-benzonitrile

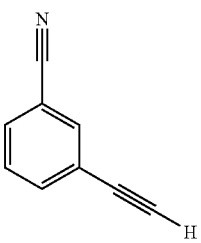

The title compound of Example 17 (9.35 g, 47.0 mmol) and potassium carbonate (32.0 g, 235.0 mmol) was stirred in MeOH (120 mL) at RT for 15 minutes. The reaction was partitioned between water and hexanes. The organic extracts were washed with water, dried over sodium sulphate, filtered and concentrated. The reaction mixture was purified by column chromatography to afford the title product (1.45 g, 56%) as a white solid.

$^1$H NMR (300 MHz, CDCl$_3$): δ (ppm) 7.78 (t, 1H), 7.71 (dd, 1H), 7.65 (dd, 1H), 7.49 (t, 1H), 3.21 (s, 1H).

| 16.2 | 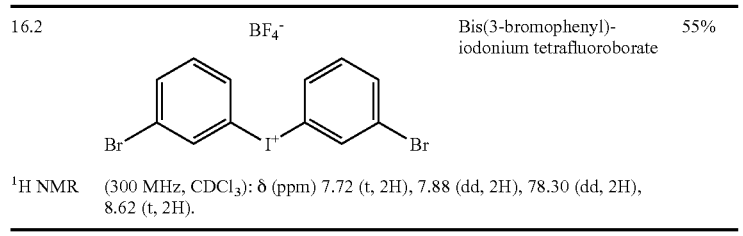 | Bis(3-bromophenyl)-iodonium tetrafluoroborate | 55% |
|---|---|---|---|
| $^1$H NMR | (300 MHz, CDCl$_3$): δ (ppm) 7.72 (t, 2H), 7.88 (dd, 2H), 78.30 (dd, 2H), 8.62 (t, 2H). | | |

Example 19.1

Pyrazine-2-carboxylic acid methyl ester

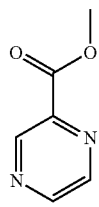

To pyrazine-2-carboxylic acid (15.0 g, 121 mmol) in DMF (150 mL) were added $K_2CO_3$ (50 g, 363 mmol) and MeI (9.0 mL, 145 mmol). After stirring for 3 days, the reaction mixture was filtered and then concentrated. The residue was dissolved in ethyl acetate, washed with water (3 times) and brine, dried over anhydrous $Na_2SO_4$, filtered and concentrated. Purification by flash column chromatography eluted with 10-30% ethyl acetate in hexanes gave the title product (1.28 g, 8%).

$^1$H NMR (300 MHz, $CDCl_3$): δ (ppm) 9.35 (s, 1H), 8.80 (s, 1H), 8.75 (s, 1H), 4.07 (s, 3H).

In a similar manner the following compound was synthesized:

| 19.2 | | | |
|---|---|---|---|
| | 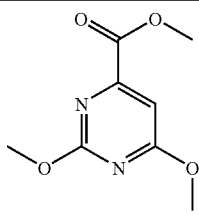 | 2,6-Dimethoxy-pyrimidine-4-carboxylic acid methyl ester | 57% |
| $^1$H NMR | (300 MHz, $CDCl_3$): δ (ppm) 7.09 (s, 1H), 4.08 (s, 3H), 4.04 (s, 3H), 3.98 (s, 3H) | | |

Example 20.1

Pyridazine-4-carboxylic acid ethyl ester

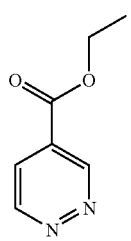

To pyridazine-4-carboxylic acid (1.0 g, 8.1 mmol) in ethanol (10 mL) was added concentrated $H_2SO_4$ (4.2 mL) and then heated at reflux for 5 hours. The reaction mixture was cooled, concentrated in vacuo and basified with saturated $Na_2CO_3$. After filtration, the aqueous was extracted with ethyl acetate, dried over anhydrous $Na_2SO_4$, filtered and concentrated to give the title product as a dark yellow oil (970 mg, 79%).

$^1$H NMR (300 MHz, $CDCl_3$): δ (ppm) 9.69 (s, 1H), 8.44 (d, 1H), 8.00 (d, 1H), 4.45 (q, 2H), 1.44 (t, 3H).

In a similar manner the following compound was synthesized:

| 20.2 | | | |
|---|---|---|---|
| | 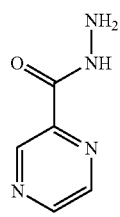 | 6-Oxo-1,6-dihydro-pyridazine-4-carboxylic acid ethyl ester | 83% |
| $^1$H NMR | (400 MHz, $CD_3OD$): δ (ppm) 8.27 (d, 1H), 7.42 (d, 1H), 4.40 (q, 2H), 1.39 (t, 3H) | | |

Example 21.1

Pyrazine-2-carbohydrazide

To the title compound of Example 19.1 (1.28 mg, 9.3 mmol) in ethanol (10 mL) was added hydrazine hydrate (0.54 mL, 11.1 mmol) and then heated at 78° C. overnight. The reaction mixture was cooled and concentrated in vacuo. The residue was triturated with ethyl acetate, filtered and dried to give the title product as a yellow solid (870 mg, 68%).

$^1$H NMR (300 MHz, $(CD_3)_2SO$): δ (ppm) 10.16 (broad s, 1H), 9.13 (s, 1H), 8.84 (s, 1H), 8.70 (s, 1H), 4.65 (broad s, 2H).

In a similar manner the following compounds were synthesized:

| 21.2 | [structure] | Pyridazine-4-carboxylic acid hydrazide | 77%<br>677 mg<br>yellow solid |
|---|---|---|---|
| $^1$H NMR | (300 MHz, CDCl$_3$): δ (ppm) 9.51 (s, 1H), 9.41 (d, 1H), 7.96 (m, 1H) | | |
| 21.3 | [structure] | Pyrimidine-5-carboxylic acid hydrazide | 92%<br>yellow solid, |
| $^1$H NMR | (300 MHz, CDCl$_3$): δ (ppm) 9.30 (s, 1H), 9.13 (s, 2H), 4.60 (br, 2H), 2.50 (br, 1H) | | |
| 21.4 | [structure] | 2,6-Dimethoxy-pyrimidine-4-carboxylic acid hydrazide | 74%<br>yellow solid |
| $^1$H NMR | (300 MHz, CDCl$_3$): δ (ppm) 10.04 (br, 1H), 6.93 (s, 1H), 4.87 (br, 2H), 3.99 (s, 3H), 3.94 (s, 3H) | | |
| 21.5 | [structure] | 2-Oxo-1,2-dihydro-pyridine-4-carboxylic acid hydrazide | Commercially available from Chemstep |
| 21.6 | [structure] | 6-Oxo-1,6-dihydro-pyridazine-4-carboxylic acid hydrazide | 99% |
| 1H NMR | (400 MHz, (CD$_3$)$_2$SO): δ (ppm) 8.05 (d, 1H), 7.09 (d, 1H), 6.40 (broad s, 4H) | | |
| 21.7 | [structure] | 1-Methyl-6-oxo-1,6-dihydro-pyridazine-3-carboxylic acid hydrazide | 89% |

| | | | |
|---|---|---|---|
| ¹H NMR | (400 MHz, (CD₃)₂SO): δ (ppm) 9.69 (s, 1H), 7.76 (d, 1H), 6.96 (d, 1H), 4.45 (s, 2H), 3.65 (s, 3H) | | |
| 21.8 | 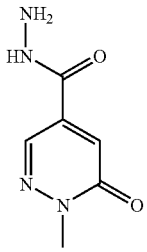 | 1-Methyl-6-oxo-1,6-dihydro-pyridazine-4-carboxylic acid hydrazide | 95% |
| ¹H NMR | (400 MHz, (CD₃)₂SO) δ 10.01 (broad s, 1H); 8.09 (d, 1H); 7.16 (d, 1H); 4.62 (broad s, 2H); 3.62 (s, 3H) | | |
| 21.09 | 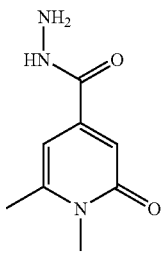 | 1,6-Dimethyl-2-oxo-1,2-dihydro-pyridine-4-carboxylic acid hydrazide | Quantitative |
| ¹H NMR | (400 MHz, (CD₃)₂SO): δ (ppm) 9.85 (broad s, 1H), 6.61 (s, 1H), 6.43 (s, 1H), 4.52 (broad s, 2H), 3.42 (s, 3H), 2.37 (s, 3H) | | |
| 21.10 | 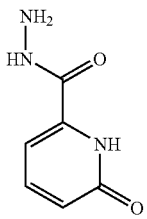 | 6-Oxo-1,6-dihydro-pyridine-2-carboxylic acid hydrazide | 89% |
| ¹H NMR | (500 MHz, (CD₃)₂SO): δ (ppm) 7.61 (dd, 1H), 7.03 (d, 1H), 6.63 (d, 1H) | | |

Example 22

4-Ethoxycarbonyl-1-methyl-pyridinium iodide

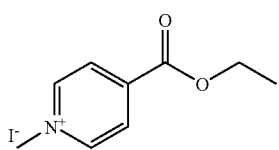

Isonicotinic acid ethyl ester (5 g, 33 mmol), was dissolved in ethanol (40 mL). Methyl iodide (4.13 mL, 66.1 mmol) was added and the clear solution was stirred overnight at 60° C. The resulting mixture was evaporated to yield a red/orange solid, which was determined by ¹H NMR and thin-layer chromatography (TLC) to be the title product in quantitative yield. The crude mixture was used directly in the following reaction.

Example 23

1-Methyl-2-oxo-1,2-dihydropyridine-4-carboxylic acid

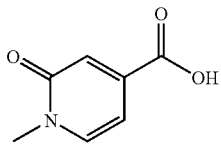

The title compound of Example 22 was dissolved in water (45 mL). Sodium hydroxide (7.92 g, 198 mmol) was dissolved in water (14 mL) and potassium ferricyanide (22.3 g, 67.6 mmol) was dissolved in water (37 mL). 2 mL aliquots of the sodium hydroxide solution and 4 mL aliquots of the potassium ferricyanide solution were added at 0.5 h intervals. After the addition of both reagents was complete the reaction was heated to 50° C. for 1 h, then cooled to room temperature and acidified with concentrated hydrochloric acid. The title product was then filtered off to be used in the subsequent reaction (2.73 g, 54%).

¹H NMR (300 MHz, CDCl₃): δ (ppm) 8.29 (d, 1H), 7.90 (dd, 1H), 6.61 (d, 1H), 3.64 (s, 3H).

Example 24

1-Methyl-2-oxo-1,2-dihydro-pyridine-4-carboxylic acid methyl ester

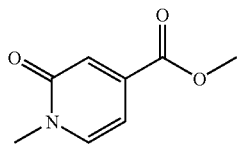

The title compound of Example 23 (2.73 g, 17.8 mmol) was dissolved in DMF (25 mL). Potassium carbonate (7.39 g, 53.5 mmol) was added, followed by iodomethane (2.22 mL, 35.6 mmol). The reaction was stirred overnight at room temperature. The reaction mixture was diluted with ethyl acetate and washed with water. The combined organics were concentrated to yield the title product, in quantitative yield.

$^1$H NMR (300 MHz, CDCl$_3$): δ (ppm) 7.35 (d, 1H), 7.19 (d, 1H), 6.65 (dd, 1H), 3.90 (s, 3H), 3.57 (s, 3H).

| 24.2 | 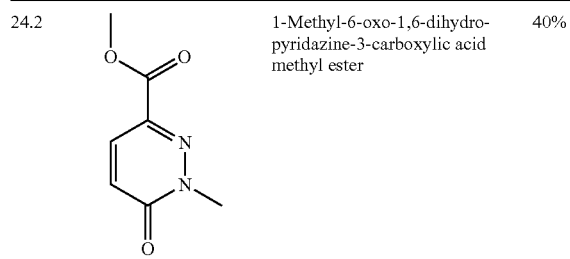 | 1-Methyl-6-oxo-1,6-dihydro-pyridazine-3-carboxylic acid methyl ester | 40% |
|---|---|---|---|
| $^1$H NMR | (400 MHz, CDCl$_3$): δ 7.86 (d, 1H), 6.95 (d, 1H), 3.97 (s, 3H), 3.88 (s, 3H) | | |

Example 25

1-methyl-2-oxo-1,2-dihydropyridine-4-carbohydrazide

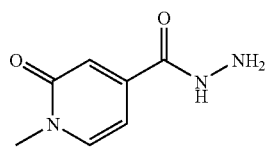

The title compound of example 24 (4.0 g, 23.9 mmol) was dissolved in ethanol (50 mL). Hydrazine hydrate (5.8 mL, 119 mmol) was added and the reaction was stirred at 78° C. for 3 hours. The reaction mixture was then cooled to room temperature and the product was filtered off to give 3.13 g (78% yield) of the title compound as a light yellow solid.

$^1$H NMR (300 MHz, CDCl$_3$, 2 rotomers): δ (ppm) 8.21-7.98 (d, 1H), 7.22-7.29 (d, 1H), 3.61-3.65 (s, 3H), 3.88-4.01 (3H), 3.98-3.06 (dd, 1H).

Example 26

1-Methyl-6-oxo-1,6-dihydro-pyridine-3-carboxylic acid

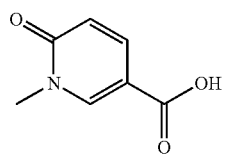

Sodium hydride (2.87 g, 60%, 71.8 mmol) was added slowly to methanol (62.5 mL) with stirring. 6-Hydroxy-nicotinic acid (5 g, 35.9 mmol) was added slowly, and the reaction mixture was heated to 62° C. Iodomethane (8.96 mL, 143.7 mmol) was added and the reaction was stirred overnight. The mixture was then cooled to room temperature and filtered to remove undissolved starting material. The filtrate was concentrated to yield a yellow powder which NMR analysis showed contained the title compound and methyl 1-methyl-6-oxo-1,6-dihydropyridine-3-carboxylate. This mixture was used in the subsequent reaction.

$^1$H NMR (300 MHz, (CD$_3$)$_2$SO): δ (ppm) 3.45 (s, 3H); 3.49 (s, 3H); 3.82 (s, 3H); 6.30 (d, 1H); 6.40 (d, 1H); 7.74-7.83 (m, 1H); 7.74-7.83 (m, 1H); 8.26 (d, 1H), 8.51 (d, 1H).

Example 27

1-Methyl-6-oxo-1,6-dihydro-pyridine-3-carboxylic acid methyl ester

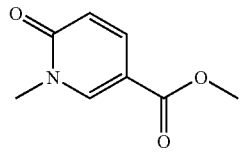

The mixture obtained in Example 26 (~2.5 g total) was dissolved in dichloromethane (30 mL). Oxalyl chloride (2 M in dichloromethane, 16.3 mL. 32.6 mmol) was added and the reaction was stirred for 30 min. The reaction was quenched with methanol, then diluted with dichloromethane and washed with water. The organic phase was dried over anhydrous magnesium sulfate, filtered and concentrated, then chromatographed in 20-50% ethyl acetate in hexanes to yield the title product 1.55 g, 26% (2 steps).

$^1$H NMR (300 MHz, CDCl$_3$): δ (ppm) 8.49 (d, 1H), 7.85 (dd, 1H), 6.54 (d, 1H), 3.86 (s, 3H), 3.60 (s, 3H).

Example 28

1-Methyl-6-oxo-1,6-dihydro-pyridine-3-carboxylic acid hydrazide

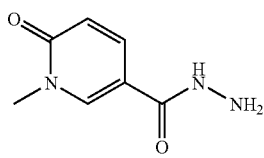

The title compound of Example 27 (775 mg, 4.64 mmol) was dissolved in ethanol (10 mL) and heated to 78° C. Hydrazine hydrate (1.12 mL, 23.2 mmol) was added and the reaction was stirred at 78° C. overnight. The reaction was then cooled to room temperature and the product (white solid) was filtered off (590 mg, 76%).

$^1$H NMR (300 MHz, $(CD_3)_2SO$): δ (ppm) 9.48 (s, broad, 1H), 8.30 (d, 1H), 7.81 (dd, 1H), 6.38 (d, 1H), 4.40 (s, broad, 2H), 3.46 (s, 3H).

Example 29

5-Methyl-2H-pyridazin-3-one

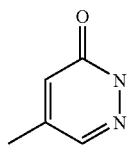

The 4,4-dimethoxy-3-methyl-but-2-enoic acid ethyl ester (Qi-Ying Hu, Pankaj D. Rege, and E. J. Corey, J. Am. Chem. Soc., 2004, 126, 5984) (82 g, 440 mmol) was mixed with hydrazine hydrate (50 g, 999 mmol) at room temperature. The mixture was heated at 60° C. for 4 h. After evaporation of solvents the oil residue was further dried under vacuum. To the resulting residue was added 6 M aq. HCl. The mixture was heated at 60° C. for 5 h. The solvents were removed in vacuo. To the residue was added methanol three times, followed by concentration. To the resulting residue was treated with dry ethanol followed by filtration to removed insoluble solid. The filtrate was concentrated to dryness. To the resulting residue was added dry i-PrOH and 20 g anhydrous $K_2CO_3$. The mixture was heated for 20 min at 60° C. After filtration, the filtrate was concentrated to dryness. The residue was purified with flash chromatography using DCM:MeOH:Et$_3$N (10:1: 0.3) to give the title compound (13.4 g, 28%).

$^1$H NMR (400 MHz, CD$_3$OD): δ (ppm) 2.24 (s, 3H), 6.73 (s, 1H), 7.82 (s, 1H).

Example 30

6-Oxo-1,6-dihydro-pyridazine-4-carboxylic acid

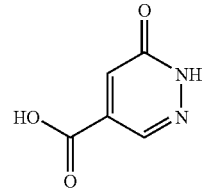

To a stirred solution of the title compound of Example 29 (4.4 g, 40 mmol) in concentrated sulphuric acid (80 mL), potassium dichromate (18 g, 61 mmol) was added in small quantities at 50-60° C. as a finely ground powder. The starting material was added to the mixture within 20 min. Stirring was continued for a further 10 min at 60° C., then the viscous green mixture was poured on crushed ice. The solid powder, which separated, was collected, washed with cold water and dried to give the title compound (4.5 g, 77%).

$^1$H NMR (400 MHz, $(CD_3)_2SO$): δ (ppm) 7.22 (s, 3H), 8.13 (s, 1H), 13.38 (s, broad, 1H).

Example 31.1

4-(5-{2-[5-(3-chloro phenyl)isoxazol-3-yl]piperidin-1-yl}-4-methyl-4H-1,2,4-triazol-3-yl)-2,6-dimethoxypyrimidine

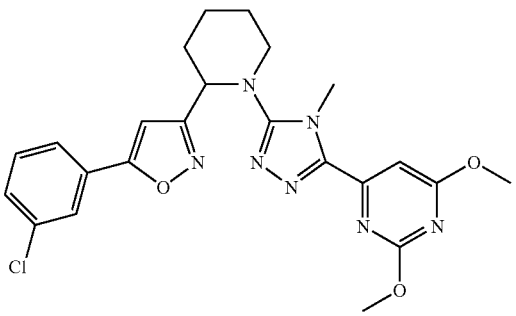

The title compound of Example 8.5 (101 mg, 0.29 mmol) and the title compound of Example 21.4 (86 mg, 0.43 mmol) in isopropanol (3 mL) in a sealed vial were heated at 100° C. for 5 days. The solvent was removed and the residue was diluted with dichloromethane. Polymer supported isocyanate was added and the mixture was stirred for three hours to remove excess 2,6-dimethoxypyrimidine-4-carbohydrazide. The mixture was filtered and the filtrate was concentrated. The crude residue was purified by flash chromatography eluted with 100% dichloromethane to 1 M methanol in dichloromethane. Yellow foam solid was obtained as the title product (336 mg, 24%).

$^1$H NMR (300 MHz, CDCl$_3$): δ (ppm) 7.68 (s, 1H), 7.58 (m, 1H), 7.35 (m, 2H), 7.34 (s, 1H), 6.52 (s, 1H), 4.79 (t, 1H), 4.01 (s, 3H), 3.99 (s, 3H), 3.92 (s, 3H), 3.28 (m, 2H), 2.19 (q, 2H), 1.86 (m, 4H)

In a similar manner the following compounds were synthesized. Enantiomerically pure products were either synthesised as racemates and separated by chiral HPLC or were synthesised from enantiomerically pure starting material. Purification by preparative chiral HPLC was performed using Chiralcel OJ, 250×20 mm, 10 μm or Chiralpak AS, 250×20 mm, 10 μm columns eluted with mixtures of EtOH/heptane/TEA or EtOH/TEA. For compounds separated by chiral HPLC the yield is given for synthesis of the racemate.

| | | | | |
|---|---|---|---|---|
| 31.2 | | | 3-{3-[(R)-1-(4-Methyl-5-pyrimidin-5-yl-4H-[1,2,4]triazol-3-yl)-pyrrolidin-2-yl]-isoxazol-5-yl}-benzonitrile | 68% White solid |
| $^1$H NMR | (300 MHz, CDCl$_3$): δ (ppm) 9.31 (s, 1H), 9.06 (s, 2H), 7.98 (m, 2H), 7.72 (d, 1H), 7.59 (t, 1H), 6.64 (s, 1H), 5.49 (t, 1H), 3.94 (m, 1H), 3.65 (s, 3H), 3.62 (m, 1H), 2.6 (m, 1H), 2.32 (m, 3H) | | | |
| 31.3 | | | 3-{5-[(R)-1-(4-Methyl-5-pyrazin-2-yl-4H-[1,2,4]triazol-3-yl)-pyrrolidin-2-yl]-tetrazol-2-yl}-benzonitrile | 73% Beige foam |
| $^1$H NMR | (300 MHz, CDCl$_3$): δ (ppm) 9.48 (s, 1H), 8.58 (s, 2H), 8.37 (m, 2H), 7.74 (m, 2H), 5.77 (t, 1H), 4 (m, 1H), 3.95 (s, 3H), 3.52 (m, 1H), 2.67 (m, 1H), 2.35 (m, 3H) | | | |
| 31.4 | | | 3-{3-[(R)-1-(4-Methyl-5-pyrazin-2-yl-4H-[1,2,4]triazol-3-yl)-pyrrolidin-2-yl]-isoxazol-5-yl}-benzonitrile | 36% Colorless foam |
| $^1$H NMR | (300 MHz, CDCl$_3$): δ (ppm) 8.81 (s, 1H), 8.55 (s, 2H), 7.98 (m, 2H), 7.7 (d, 1H), 7.57 (t, 1H), 6.62 (s, 1H), 5.53 (t, 1H), 4.14 (s, 1H), 3.98 (m, 1H), 3.93 (s, 3H), 2.59 (m, 1H), 2.28 (m, 3H) | | | |
| 31.5 | | | 5-(5-{(R)-2-[2-(3-Chloro-phenyl)-2H-tetrazol-5-yl]-pyrrolidin-1-yl}-4-methyl-4H-[1,2,4]triazol-3-yl)-pyrimidine | 52% Pale yellow solid |
| $^1$H NMR | (300 MHz, CDCl$_3$): δ (ppm) 9.3 (s, 1H), 9.06 (s, 1H), 8.13 (s, 1H), 8.02 (m, 2H), 7.49 (m, 2H), 5.73 (m, 1H), 4.01 (m, 1H), 3.69 (s, 3H), 3.59 (m, 1H), 2.43 (m, 4H) | | | |

| | | | |
|---|---|---|---|
| 31.6 | 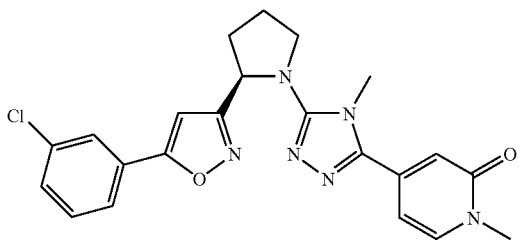 | 4-(5-{(R)-2-[5-(3-Chloro-phenyl)-isoxazol-3-yl]-pyrrolidin-1-yl}-4-methyl-4H-[1,2,4]triazol-3-yl)-1-methyl-1H-pyridin-2-one | 51% Chiral separation |
| $^1$H NMR | (500 MHz, CDCl$_3$): δ (ppm) 7.70 (m, 1H), 7.60 (m, 1H), 7.36 (m, 3H), 6.76 (dd, 1H), 6.66 (d, 1H), 6.50 (s, 1H), 5.43 (t, 1H), 3.89 (ddd, 1H), 3.62 (m, 3H), 3.57 (s, 3H), 3.50 (m, 1H), 2.55 (m, 1H), 2.30 (m, 1H), 2.19 (m, 2H) | | |
| 31.7 | 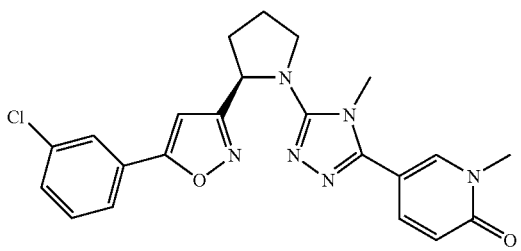 | 5-(5-{(R)-2-[5-(3-Chloro-phenyl)-isoxazol-3-yl]-pyrrolidin-1-yl}-4-methyl-4H-[1,2,4]triazol-3-yl)-1-methyl-1H-pyridin-2-one | 44% Chiral separation |
| $^1$H NMR | (500 MHz, CDCl$_3$): δ (ppm) 7.76 (d, 1H), 7.69-7.71 (m, 1H), 7.61 (dt, 1H), 7.45 (dd, 1H), 7.35-7.40 (m, 2H), 6.64 (d, 1H), 6.50 (s, 1H), 5.33 (dd, 1H), 3.83-3.89 (m, 1H), 3.59 (s, 3H), 3.49-3.52 (m, 1H), 3.49 (s, 3H), 2.52-2.59 (m, 1H), 2.12-2.32 (m, 3H) | | |
| 31.8 | 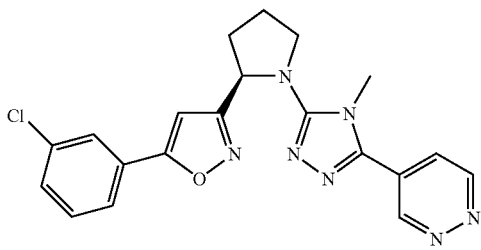 | 4-(5-{(R)-2-[5-(3-Chloro-phenyl)-isoxazol-3-yl]-pyrrolidin-1-yl}-4-methyl-4H-[1,2,4]triazol-3-yl)-pyridazine | 65% Chiral separation |
| $^1$H NMR | (500 MHz, CDCl$_3$): δ (ppm) 9.51-9.53 (m, 1H), 9.30 (dd, 1H), 7.77 (dd, 1H), 7.69-7.71 (m, 1H), 7.60 (dt, 1H), 7.34-7.40 (m, 2H), 6.51 (s, 1H), 5.44 (dd, 1H), 3.90-3.96 (m, 1H), 3.67 (s, 3H), 3.53-3.59 (m, 1H), 2.54-2.62 (m, 1H), 2.35-2.57 (m, 3H) | | |
| 31.9 | 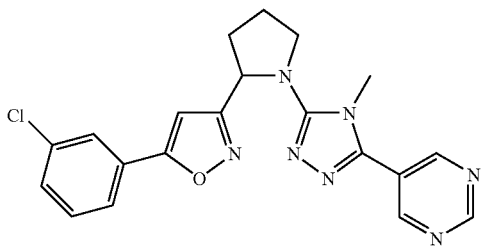 | (+/−) 5-(5-{2-[5-(3-Chloro-phenyl)-isoxazol-3-yl]-pyrrolidin-1-yl}-4-methyl-4H-[1,2,4]triazol-3-yl)-pyrimidine | 6% |
| $^1$H NMR | (500 MHz, CDCl$_3$): δ (ppm) 9.27 (s, 1H), 9.03 (s, 2H), 7.71 (m, 1H), 7.61 (dt, 1H), 7.35-7.40 (m, 2H), 6.52 (s, 1H), 5.42 (dd, 1H), 3.90 (dt, 1H), 3.61 (s, 3H), 3.55 (m, 1H), 2.57 (m, 1H), 2.14-2.34 (m, 3H) | | |

| | | | |
|---|---|---|---|
| 31.10 | 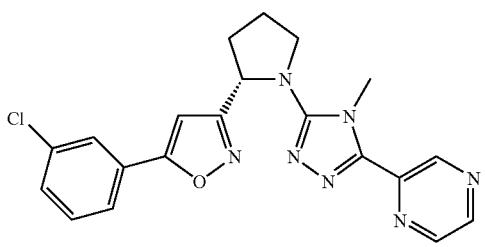 | 2-(5-{(S)-2-[5-(3-Chloro-phenyl)-isoxazol-3-yl]-pyrrolidin-1-yl}-4-methyl-4H-[1,2,4]triazol-3-yl)-pyrazine | 36% Chiral separation |
| ¹H NMR | (500 MHz, CDCl₃): δ (ppm) 9.48 (s, 1H), 8.53 (m, 2H), 7.70 (m, 1H), 7.60 (m, 1H), 7.36 (m, 2H), 6.52 (s, 1H), 5.48 (t, 1H), 3.91 (m, 4H), 3.50 (m, 1H), 2.56 (m, 1H), 2.32 (m, 1H), 2.19 (m, 2H) | | |
| 31.11 | 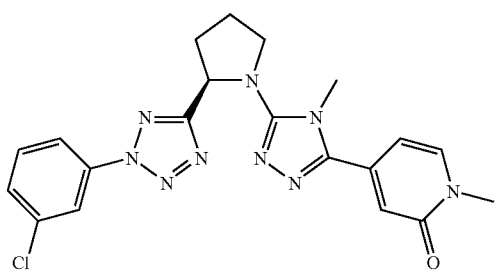 | 4-(5-{(R)-2-[2-(3-Chloro-phenyl)-2H-tetrazol-5-yl]-pyrrolidin-1-yl}-4-methyl-4H-[1,2,4]triazol-3-yl)-1-methyl-1H-pyridin-2-one | 36% |
| ¹H NMR | (300 MHz, CDCl₃): δ (ppm) 8.40 (s, 1H), 8.00 (m, 1H), 7.47 (m, 2H), 7.36 (d, 1H), 6.76 (dd, 1H), 6.69 (d, 1H), 5.72 (dd, 1H), 3.96 (m, 1H), 3.68 (s, 3H), 3.58 (s, 3H), 3.53 (m, 1H), 2.61 (m, 1H), 2.31 (m, 3H) | | |
| 31.12 | 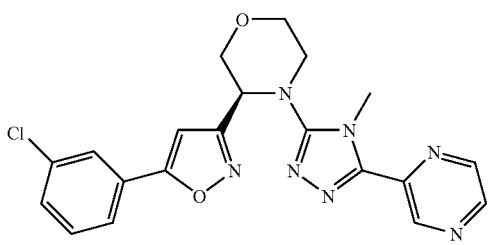 | (S)-3-[5-(3-Chloro-phenyl)-isoxazol-3-yl]-4-(4-methyl-5-pyrazon-2-yl-4H-[1,2,4]triazol-3-yl)-morpholine | Chiral separation |
| ¹H NMR | (400 MHz, CDCl₃): δ (ppm) 9.48 (s, 1H), 8.63-8.54 (m, 2H), 7.71-7.67 (m, 1H), 7.62-7.56 (m, 1H), 7.74-7.33 (m, 2H), 6.67 (s, 1H), 5.00-4.94 (m, 1H), 4.25 (dd, 1H), 4.13-3.90 (m, 3H), 3.99 (s, 3H), 3.57-3.48 (m, 1H), 3.46-3.35 (m, 1H) | | |
| 31.13 | 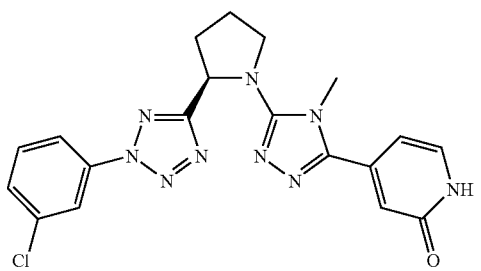 | 4-(5-{(R)-2-[2-(3-Chloro-phenyl)-2H-tetrazol-5-yl]-pyrrolidin-1-yl}-4-methyl-4H-[1,2,4]triazol-3-yl)-1H-pyridin-2-one | 80% |
| ¹H NMR | (300 MHz, CDCl₃): δ (ppm) 8.12 (s, 1H), 8 (m, 1H), 7.44 (m, 3H), 6.85 (t, 1H), 6.72 (q, 1H), 5.73 (s, 1H), 3.98 (m, 1H), 3.69 (m, 3H), 3.56 (m, 1H), 2.62 (s, 1H), 2.31 (m, 3H) | | |

| | | | |
|---|---|---|---|
| 31.14 | 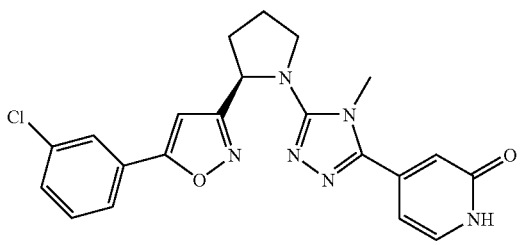 | 4-(5-{(R)-2-[5-(3-Chloro-phenyl)-isoxazol-3-yl]-pyrrolidin-1-yl}-4-methyl-4H-[1,2,4]triazol-3-yl)-1H-pyridin-2-one | Isolated in Example 31.6 |
| $^1$H NMR | (500 MHz, (CD$_3$)$_2$SO): δ (ppm) 11.70 (s, broad, 1H), 7.91-7.89 (m, 1H), 7.81-7.75 (m, 1H), 7.56-7.51 (m, 2H), 7.45 (d, 1H), 7.14 (s, 1H), 6.54 (d, 1H), 6.47 (dd, 1H), 5.29 (t, 1H), 3.84-3.78 (m, 1H), 3.59 (s, 3H), 3.48-3.42 (m, 1H), 2.48-2.40 (m, 1H), 2.15-1.96 (m, 3H) | | |
| 31.15 | 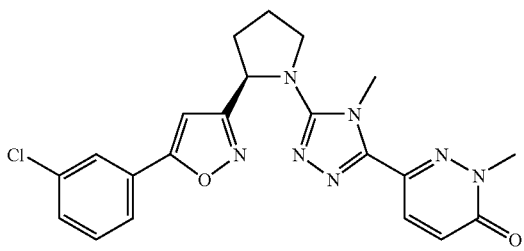 | 6-(5-{(R)-2-[5-(3-Chloro-phenyl)-isoxazol-3-yl]-pyrrolidin-1-yl}-4-methyl-4H-[1,2,4]triazol-3-yl)-2-methyl-2H-pyridazin-3-one | 77% |
| $^1$H NMR | (400 MHz, CDCl$_3$): δ 8.09 (ppm) (d, 1H), 7.68 (s, 1H), 7.57 (m, 1H), 7.34 (m, 2H), 6.97 (d, 1H), 6.53 (s, 1H), 5.48 (t, 1H), 3.92 (m, 1H), 3.81 (s, 3H), 3.79 (s, 3H), 3.50 (m, 1H), 2.54 (m, 1H), 2.22 (m, 3H) | | |
| 31.16 | 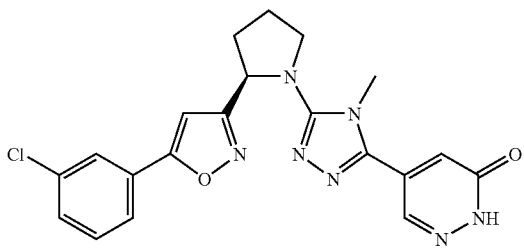 | 5-(5-{(R)-2-[5-(3-Chloro-phenyl)-isoxazol-3-yl]-pyrrolidin-1-yl}-4-methyl-4H-[1,2,4]triazol-3-yl)-2H-pyridazin-3-one | 56% |
| $^1$H NMR | (400 MHz, CDCl$_3$): δ (ppm) 11.30 (broad s, 1H), 8.32 (s, 1H), 7.67 (s, 1H), 7.57 (m, 1H), 7.35 (m, 2H), 7.01 (s, 1H), 6.58 (s, 1H), 5.57 (s, 1H), 3.96 (m, 1H), 3.70 (s, 3H), 3.65 (m, 1H), 2.55 (m, 1H), 2.20 (m, 3H) | | |
| 31.17 | 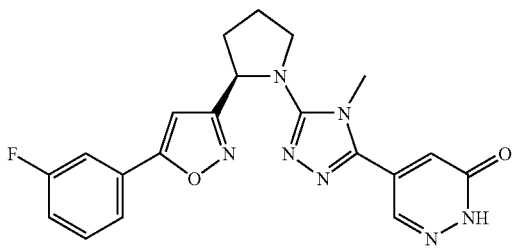 | 5-(5-{(R)-2-[5-(3-Fluoro-phenyl)-isoxazol-3-yl]-pyrrolidin-1-yl}-4-methyl-4H-[1,2,4]triazol-3-yl)-2H-pyridazin-3-one | 48% |
| $^1$H NMR | (400 MHz, CDCl$_3$): δ 11.30 (broad s, 1H), 8.35 (s, 1H), 7.47 (d, 1H), 7.37 (m, 2H), 7.07 (m, 1H), 6.99 (s, 1H), 6.54 (s, 1H), 5.52 (m, 1H), 3.94 (m, 1H), 3.67 (s, 3H), 3.60 (m, 1H), 2.55 (m, 1H), 2.20 (m, 3H) | | |
| 31.18 | 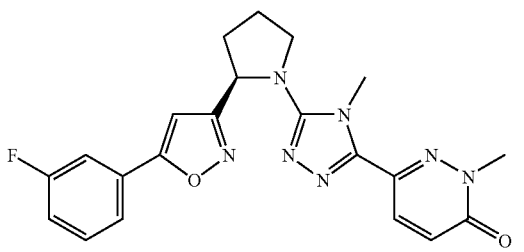 | 6-(5-{(R)-2-[5-(3-Fluoro-phenyl)-isoxazol-3-yl]-pyrrolidin-1-yl}-4-methyl-4H-[1,2,4]triazol-3-yl)-2-methyl-2H-pyridazin-3-one | 62% |

| | | | |
|---|---|---|---|
| ¹H NMR | (400 MHz, CDCl₃): δ (ppm) 8.08 (d, 1H), 7.47 (d, 1H), 7.37 (m, 2H), 7.08 (t, 1H), 6.96 (d, 1H), 6.52 (s, 1H), 5.48 (t, 1H), 3.91 (m, 1H), 3.81 (s, 3H), 3.79 (s, 3H), 3.50 (m, 1H), 2.54 (m, 1H), 2.19 (m, 3H) | | |
| 31.19 | 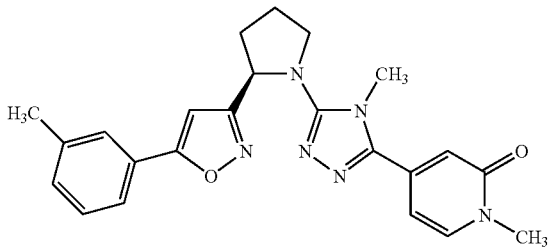 | 1-Methyl-4-{4-methyl-5-[(R)-2-(5-m-tolylisoxazol-3-yl)pyrrolidin-1-yl]-4H-[1,2,4]triazol-3-yl}-1H-pyridin-2-one | 52% |
| ¹H NMR | (500 MHz, CDCl₃): δ (ppm) 7.52 (m, 2H), 7.35 (d, 1H), 7.30 (t, 1H), 7.20 (d, 1H), 6.74 (dd, 1H), 6.65 (broad s, 1H), 6.45 (s, 1H), 5.40 (t, 1H), 3.88 (m, 1H), 3.60 (s, 3H), 3.56 (s, 3H), 3.51 (m, 1H), 2.53 (m, 1H), 2.37 (s, 3H), 2.28 (m, 1H), 2.24-2.10 (m, 2H) | | |
| 31.20 | 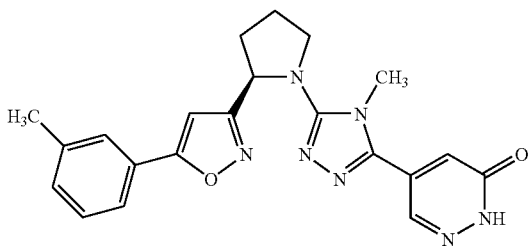 | 5-{4-Methyl-5-[(R)-2-(5-m-tolyl-isoxazol-3-yl)-pyrrolidin-1-yl]-4H-[1,2,4]triazol-3-yl}-2H-pyridazin-3-one | 20% |
| ¹H NMR | (500 MHz, CDCl₃): δ (ppm) 10.9 (broad s, 1H), 8.43 (d, 1H), 7.52 (m, 2H), 7.31 (m, 1H), 7.22 (d, 1H), 6.97 (d, 1H), 6.44 (s, 1H), 5.42 (t, 1H), 3.93 (ddd, 1H), 3.65 (s, 3H), 3.56 (m, 1H), 2.57 (m, 1H), 2.39 (s, 3H), 2.34-2.14 (m, 3H) | | |
| 31.21 | 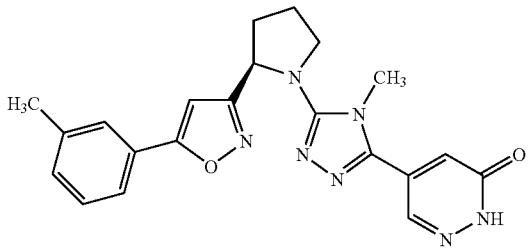 | 4-(5-{(R)-2-[5-(3-Fluoro-phenyl)-isoxazol-3-yl]-pyrrolidin-1-yl}-4-methyl-4H-[1,2,4]triazol-3-yl)-1H-pyridin-2-one | 98% |
| ¹H NMR | (500 MHz, CDCl₃): δ (ppm) 7.51-7.47 (m, 1H) 7.44-7.37 (m, 3H), 7.13-7.07 (m, 1H), 6.83 (dd, 1H), 671-6.68 (m, 1H), 6.50 (s, 1H), 5.44 (t, 1H), 3.94-3.87 (m, 1H), 3.63 (s, 3H), 3.55-3.48 (m, 1H), 2.60-2.51 (m, 1H), 2.35-2.13 (m, 3H) | | |
| 31.22 | 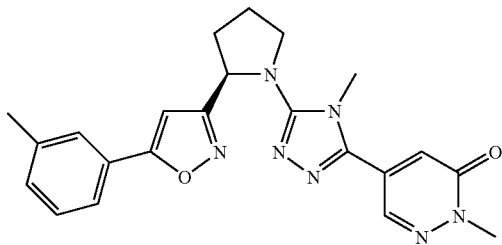 | 2-Methyl-5-{4-methyl-5-[(R)-2-(5-m-tolyl-isoxazol-3-yl)-pyrrolidin-1-yl]-4H-[1,2,4]triazol-3-yl}-2H-pyridazin-3-one | 42% |
| ¹H NMR | (500 MHz, CDCl₃): δ (ppm) 8.37 (d, 1H), 7.51 (m, 2H), 7.31 (t, 1H), 7.22 (bd, 1H), 6.94 (d, 1H), 6.44 (s, 1H), 5.41 (t, 1H), 3.92 (m, 1H), 3.81 (s, 3H), 3.63 (s, 3H), 3.55 (m, 1H), 2.55 (m, 1H), 2.38 (s, 3H), 2.35-2.13 (m, 3H) | | |

| | | | |
|---|---|---|---|
| 31.23 | 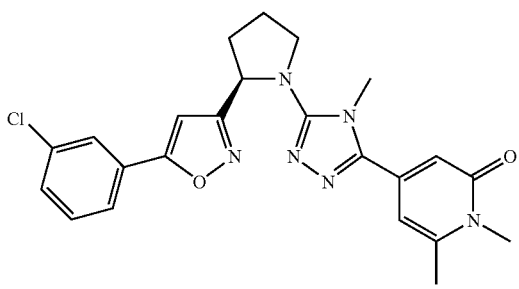 | 4-(5-{(R)-2-[5-(3-Chloro-phenyl)-isoxazol-3-yl]-pyrrolidin-1-yl}-4-methyl-4H-[1,2,4]triazol-3-yl)-1,6-dimethyl-1H-pyridin-2-one | 83% |
| ¹H NMR | (500 MHz, CDCl₃): δ (ppm) 7.70 (m, 1H), 7.60 (m, 1H), 7.37 (m, 2H), 6.65 (d, 1H), 6.55 (d, 1H), 6.50 (s, 1H), 5.43 (t, 1H), 3.88 (m, 1H), 3.60 (s, 3H), 3.55 (s, 3H), 3.49 (m, 1H), 2.54 (m, 1H), 2.40 (s, 3H), 2.31 (m, 1H), 2.25-2.12 (m, 2H) | | |
| 31.24 | 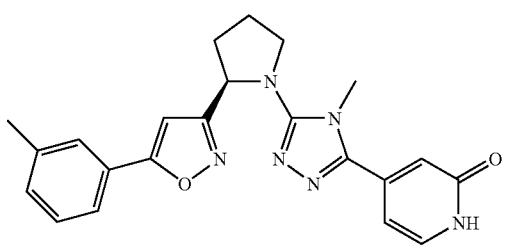 | 4-{4-Methyl-5-[(R)-2-(5-m-tolyl-isoxazol-3-yl)-pyrrolidin-1-yl]-4H-[1,2,4]triazol-3-yl}-1H-pyridin-2-one | 70% |
| ¹H NMR | (500 MHz, CDCl₃): δ (ppm) 12.68 (broad s, 1H), 7.51 (m, 2H), 7.41 (d, 1H), 7.30 (t, 1H), 7.21 (d, 1H), 6.81 (dd, 1H), 6.69 (d, 1H), 6.45 (s, 1H), 5.42 (t, 1H), 3.91 (m, 1H), 3.61 (s, 3H), 3.54 (m, 1H), 2.55 (m, 1H), 2.38 (s, 3H), 2.33-2.12 (m, 3H) | | |
| 31.25 | 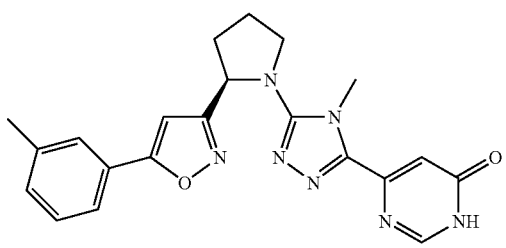 | 6-{4-Methyl-5-[(R)-2-(5-m-tolyl-isoxazol-3-yl)-pyrrolidin-1-yl]-4H-[1,2,4]triazol-3-yl}-3H-pyrimidin-4-one | 13% |
| ¹H NMR | (500 MHz, CDCl₃): δ (ppm) 8.20 (s, 1H), 7.51 (m, 2H), 7.32 (s, 1H), 7.30 (t, 1H), 7.20 (bd, 1H), 6.46 (s, 1H), 5.44 (t, 1H), 3.90 (m, 1H), 3.82 (s, 3H), 3.51 (m, 1H), 2.54 (m, 1H), 2.38 (s, 3H), 2.30 (m, 1H), 2.18 (m, 2H) | | |
| 31.26 | 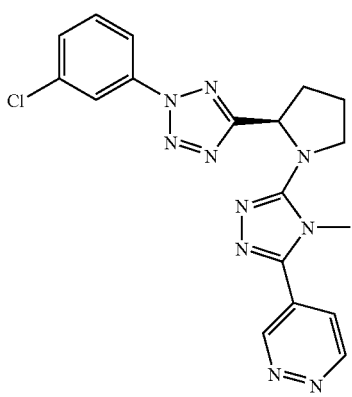 | 4-(5-{(R)-2-[2-(3-Chloro-phenyl)-2H-tetrazol-5-yl]-pyrrolidin-1-yl}-4-methyl-4H-[1,2,4]triazol-3-yl)-pyridazine | 90% |
| ¹H NMR | (500 MHz, CDCl₃): δ (ppm) 9.54 (s, 1H), 9.31 (d, 1H), 8.11 (s, 1H), 8.02-7.99 (m, 1H) 7.81-7.79 (m, 1H), 7.48-7.46 (m, 2H), 5.74 (q, 1H), 4.00 (q, 1H), 3.63-3.55 (m, 1H), 2.66-2.62 (m, 1H), 2.44-2.26 (m, 3H), 0.90-0.84 (m, 1H) | | |

| | | | |
|---|---|---|---|
| 31.27 | 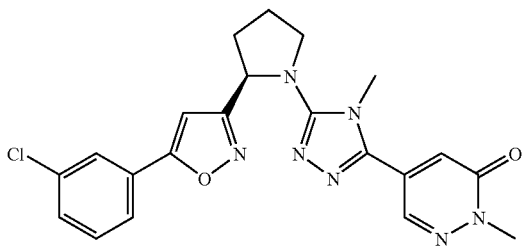 | 5-(5-{(R)-2-[5-(3-Chlorophenyl)isoxazol-3-yl]-pyrrolidin-1-yl}-4-methyl-4H-[1,2,4]triazol-3-yl)-2-methyl-2H-pyridazin-3-one | 77% |
| ¹H NMR | (400 MHz, CDCl₃): δ (ppm) 8.33 (d, 1H), 7.67 (m, 1H), 7.57 (m, 1H), 7.35 (m, 2H), 6.95 (d, 1H), 6.51 (s, 1H), 5.48 (t, 1H), 3.92 (q, 1H), 3.79 (s, 3H), 3.63 (s, 3H), 3.55 (m, 1H), 2.54 (m, 1H), 2.28-2.15 (m, 3H) | | |
| 31.28 | 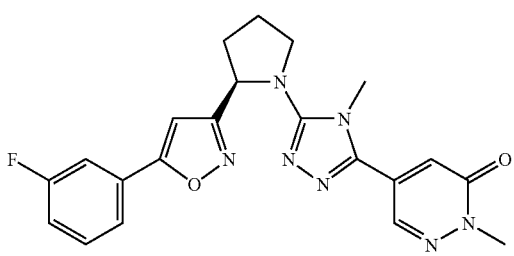 | 5-(5-{(R)-2-[5-(3-Fluorophenyl)isoxazol-3-yl]-pyrrolidin-1-yl}-4-methyl-4H-[1,2,4]triazol-3-yl)-2-methyl-2H-pyridazin-3-one | 72% |
| ¹H NMR | (400 MHz, (CD₃)₂SO): δ (ppm) 8.34 (d, 1H), 7.47 (d, 1H), 7.40-7.37 (m, 2H), 7.09 (dt, 1H), 6.94 (d, 1H), 6.49 (s, 1H), 5.45 (t, 1H), 3.92 (q, 1H), 3.79 (s, 3H), 3.63 (s, 3H), 3.52 (m, 1H), 2.54 (m, 1H), 2.33-2.10 (m, 3H) | | |
| 31.29 | 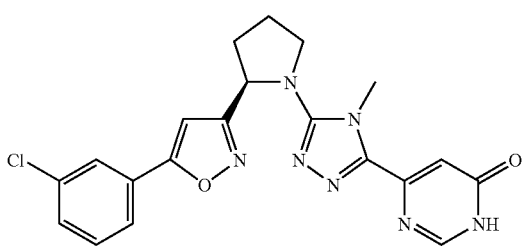 | 6-(5-{(R)-2-[5-(3-Chlorophenyl)isoxazol-3-yl]-pyrrolidin-1-yl}-4-methyl-4H-[1,2,4]triazol-3-yl)-3H-pyrimidin-4-one | 7% |
| ¹H NMR | (400 MHz, CDCl₃): δ (ppm) 8.23 (s, 1H), 7.70 (s, 1H), 7.60 (m, 1H), 7.34 (m, 2H), 6.90 (s, 1H), 6.73 (s, 1H), 5.82 (m, 1H), 4.07 (m, 1H), 3.92 (s, 4H), 2.63 (m, 1H), 2.22 (m, 3H) | | |
| 31.30 | 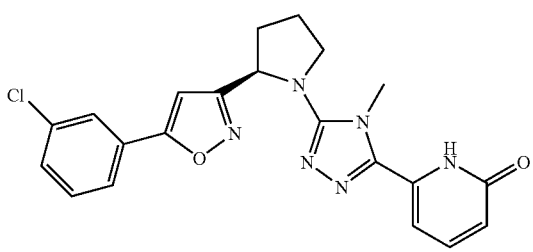 | 6-(5-{(R)-2-[5-(3-Chloro-phenyl)-isoxazol-3-yl]-pyrrolidin-1-yl}-4-methyl-4H-[1,2,4]triazol-3-yl)-1H-pyridin-2-one | 58% |
| ¹H NMR | (500 MHz, CDCl₃): δ (ppm) 9.76 (1H, broad s), 7.71-7.69 (1H, m), 7.61-7.58 (1H, m), 7.45-7.34 (3H, m), 6.62 (1H, dd, J=9, 1Hz), 6.48 (1H, s), 6.43 (1H, dd, J=7, 1Hz), 5.39 (1H, t, J=7Hz), 3.92-3.86 (1H, m), 3.68 (3H, s), 3.54-3.48 (1H, m), 2.61-2.53 (1H, m), 2.34-2.13 (3H, m) | | |

| | | | |
|---|---|---|---|
| 31.31 | 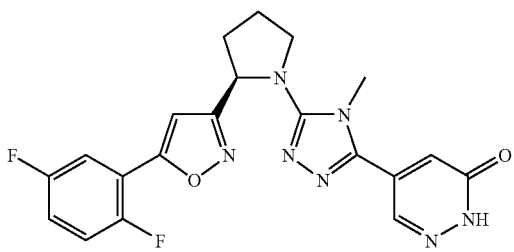 | 5-(5-{(R)-2-[5-(2,5-Difluoro-phenyl)-isoxazol-3-yl]-pyrrolidin-1-yl}-4-methyl-4H-[1,2,4]triazol-3-yl)-2H-pyridazin-3-one | 61% |
| ¹H NMR | (500 MHz, CDCl₃): δ (ppm) 8.16 (d, 1H), 7.69 (m, 1H), 7.47 (m, 1H), 7.40 (m, 1H), 7.02 (s, 1H), 6.92 (d, 1H), 5.31 (t, 1H), 3.85 (m, 1H), 3.62 (s, 3H), 3.42 (m, 1H), 2.43 (m, 1H), 2.00-2.11 (m, 3H) | | |
| 31.32 | 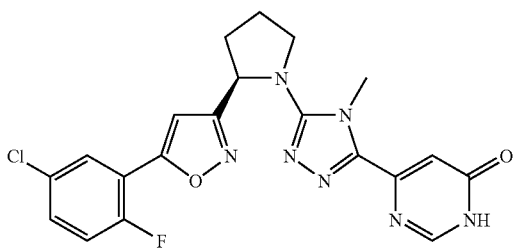 | 6-(5-{(R)-2-[5-(5-Chloro-2-fluoro-phenyl)-isoxazol-3-yl]-pyrrolidin-1-yl}-4-methyl-4H-1,2,4-triazol-3-yl)-3H-pyrimidin-4-one | 8% |
| ¹H NMR | (500 MHz, (CD₃)₂SO): δ (ppm) 8.27 (s, 1H), 7.88 (m, 1H), 7.59 (m, 1H), 7.44 (m, 1H), 6.91 (m, 1H), 6.75 (s, 1H), 5.30 (m, 1H), 3.81 (m, 1H), 3.71 (s, 3H), 3.40 (m, 1H), 2.42 (m, 1H), 2.02 (m, 3H) | | |
| 31.33 | 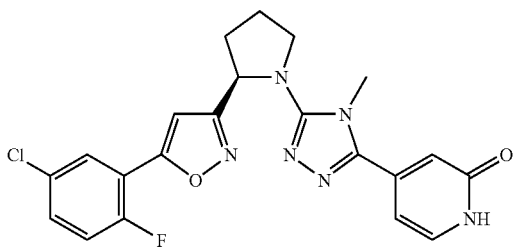 | 4-(5-{(R)-2-[5-(5-Chloro-2-fluoro-phenyl)-isoxazol-3-yl]-pyrrolidin-1-yl}-4-methyl-4H-[1,2,4]triazol-3-yl)-1H-pyridin-2-one | 49% |
| ¹H NMR | (500 MHz, (CD₃)₂SO): δ (ppm) 7.89 (m, 1H), 7.59 (m, 1H), 7.46 (m, 2H), 6.94 (m, 1H), 6.51 (m, 1H), 6.45 (m, 1H), 5.29 (m, 1H), 3.82 (m, 1H), 3.56 (s, 3H), 3.43 (m, 1H), 2.42 (m, 1H), 1.99-2.09 (m, 3H) | | |
| 31.34 | 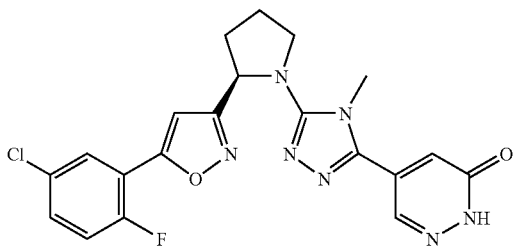 | 5-(5-{(R)-2-[5-(5-Chloro-2-fluoro-phenyl)-isoxazol-3-yl]-pyrrolidin-1-yl}-4-methyl-4H-[1,2,4]triazol-3-yl)-2H-pyridazin-3-one | 51% |
| ¹H NMR | (500 MHz, (CD₃)₂SO): δ (ppm) 8.17 (m, 1H), 7.90 (m, 1H), 7.60 (m, 1H), 7.46 (m, 1H), 7.03 (m, 1H), 6.96 (m, 1H), 5.31 (t, 1H), 3.84 (m, 1H), 3.61 (s, 3H), 3.43 (m, 1H), 2.43 (m, 1H), 1.98-2.09 (m, 3H) | | |

| | | | |
|---|---|---|---|
| 31.35 | 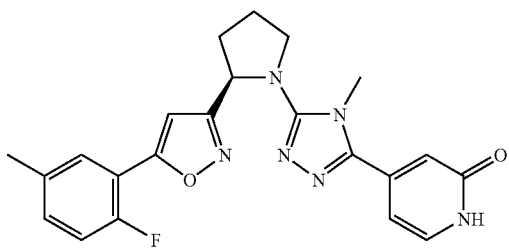 | 4-(5-{(R)-2-[5-(2-Fluoro-5-methyl-phenyl)-isoxazol-3-yl]-pyrrolidin-1-yl}-4-methyl-4H-[1,2,4]triazol-3-yl)-1H-pyridin-2-one | 55% |
| $^1$H NMR | (500 MHz, (CD$_3$)$_2$SO): δ (ppm) 7.66 (m, 1H), 7.43 (m, 1H), 7.32 (m, 1H), 7.26 (m, 1H), 6.79 (d, 1H), 6.51 (s, 1H), 6.45 (m, 1H), 5.28 (t, 1H), 3.81 (m, 1H), 3.56 (s, 3H), 3.42 (m, 1H), 2.42 (m, 1H), 2.31 (s, 3H), 1.98-2.09 (m, 3H). | | |
| 31.36 | 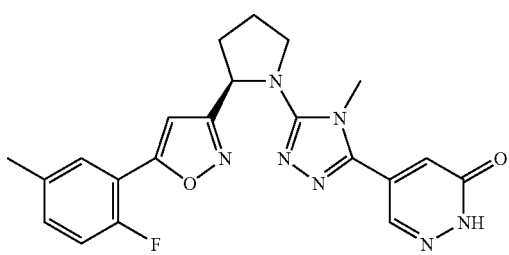 | 5-(5-{(R)-2-[5-(2-Fluoro-5-methyl-phenyl)-isoxazol-3-yl]-pyrrolidin-1-yl}-4-methyl-4H-[1,2,4]triazol-3-yl)-2H-pyridazin-3-one | 38% |
| $^1$H NMR | (500 MHz, (CD$_3$)$_2$SO): δ (ppm) 8.17 (d, 1H), 7.66 (m, 1H), 7.32 (m, 1H), 7.26 (m, 1H), 7.02 (s, 1H), 6.81 (d, 1H), 5.30 (t, 1H), 3.85 (m, 1H), 3.61 (s, 3H), 3.43 (m, 1H), 2.43 (m, 1H), 2.32 (s, 3H), 2.04 (m, 3H). | | |

Example 32

1-Methyl-6-oxo-1,6-dihydro-pyridazine-4-carboxylic acid ethyl ester

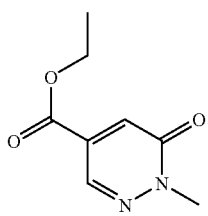

To a stirred solution of 6-oxo-1,6-dihydro-pyridazine-4-carboxylic acid ethyl ester (1.0 g, 5.9 mmol) in anhydrous DMF (15 mL) was added potassium carbonate (3.29 g, 23.8 mmol). The reaction mixture was cooled to 0° C. and methyl iodide (1.0 mL, 16 mmol) was added dropwise. The reaction mixture was allowed to reach room temperature and was then heated at 60° C. for 15 minutes. The reaction was cooled to below 0° C. and ethyl acetate and water were added. The organic layer was separated, washed with cold water and brine, dried over anhydrous sodium sulfate and concentrated. The residue was purified by RP-HPLC using a linear gradient of acetonitrile in 0.1 M ammonium acetate buffer to afford the title compound (712 mg, 66%).

$^1$H NMR (500 MHz, CDCl$_3$): δ (ppm) 8.17 (d, 1H), 7.46 (d, 1H), 4.39 (q, 2H), 3.80 (s, 3H), 1.38 (t, 3H).

Example 33.1

6-Methyl-2-oxo-1,2-dihydro-pyridine-4-carboxylic acid methyl ester

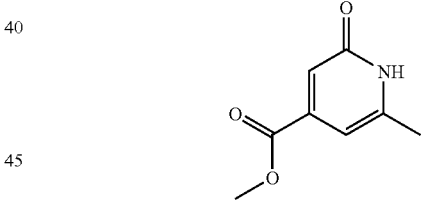

1,6-Dimethyl-2-oxo-1,2-dihydro-pyridine-4-carboxylic acid (1.0 g, 6.5 mmol) was suspended in dry methanol (8 mL) and chlorotrimethylsilane (2.8 g, 26 mmol) was added at room temperature. The reaction was stirred for 36 hours at room temperature. The solvent was removed under reduced pressure and the residue was dissolved in a mixture of dichloromethane/methanol (25 mL) and saturated aqueous sodium bicarbonate (25 mL) was added. A precipitate formed which was filtered off and washed with water and MTBE and air-dried. The filtrate was diluted with methanol/dichloromethane and water and the layers were separated. The aqueous layer was extracted once more with dichloromethane. The combined organic layers were dried (sodium sulfate), filtered and concentrated. Both the previously precipitated material and the concentrated organic layer consisted of product and were combined to afford of the title compound (820 mg, 75%).

$^1$H NMR (400 MHz, (CD$_3$)$_2$SO): δ (ppm) 11.99 (broad s, 1H), 6.62 (s, 1H), 6.35 (s, 1H), 3.82 (s, 3H), 2.22 (s, 3H).

Example 33.2

Pyridazine-4-carboxylic acid ethyl ester

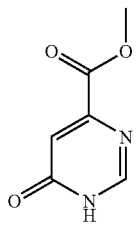

To 6-pyrimidine-4-carboxylic acid (36.0 g, 257 mmol) in methanol (360 mL) was dropwise added chlorotrimethylsilane (56 g, 554 mmol) and then stirred for 8 hours at room temperature. The solvent was evaporated off and the solid was refluxed with 200 mL methanol for 30 minutes. The reaction mixture was cooled, the precipitated solid was filtered off and washed with a small amount of methanol and dried under vacuum at 35° C. to afford 27.9 g (70%) of the title compound.

$^1$H NMR (300 MHz, (CD$_3$)$_2$SO): δ (ppm) 12.50 (broad s, 1H), 8.23 (s, 1H), 6.83 (s, 1H), 3.80 (s, 3H).

Example 34

1,6-Dimethyl-2-oxo-1,2-dihydro-pyridine-4-carboxylic acid methyl ester

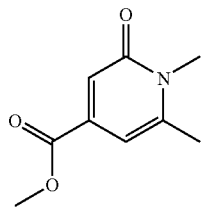

A suspension of the title compound of Example 33.1 (0.80 g, 4.8 mmol) and dimethylformamide dimethylacetal (3.2 mL, 24 mmol) in DMF (10 mL) was heated at 60° C. for 48 hours. The reaction mixture was concentrated and the residue was dissolved in dichloromethane and washed with water. The organic layer was concentrated. Recrystallization from ethyl acetate/heptane afforded the title compound (423 mg, 49%)

$^1$H-NMR (400 MHz, CDCl$_3$): δ (ppm) 7.07 (d, 1H), 6.54 (d, 1H), 3.89 (s, 3H), 3.54 (s, 3H), 2.40 (s, 3H).

Example 35

6-Oxo-1,6-dihydro-pyridine-2-carboxylic acid methyl ester

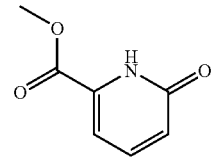

6-Oxo-1,6-dihydro-pyridine-2-carboxylic acid (1.20 g, 8.63 mmol) was suspended in HCl-bubbled methanol (10 mL). The reaction mixture was heated in a microwave oven to 100° C. for 15 minutes before it was concentrated under reduced pressure. Toluene (50 mL) was added and the mixture was concentrated under reduced pressure. To the residue was added EtOAc (20 mL) and water (15 mL) before pH was adjusted to around 5 with saturated NaHCO$_3$—solution. Most of the product was found to be in the water phase and for that reason EtOAc was evaporated under reduced pressure. The product was extracted with DCM (20 mL+3×10 mL). The combined organic phases were dried over magnesium sulphate, filtered and concentrated under reduced pressure to give the title compound as an off-white powder (1.17 g, 89%).

$^1$H NMR (500 MHz, CD$_3$)$_2$SO): δ (ppm) 11.50 (1NH, broad s), 7.63 (dd, 1H), 7.15 (d, 1H), 6.72 (d, 1H), 3.83 (3H, s).

Example 36.1

Acetic acid 2,2,2-trichloro-1-(2,5-difluoro-phenyl)-ethyl ester

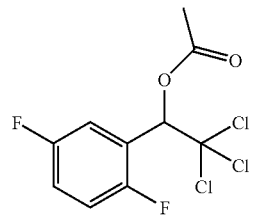

2,5-Difluoro-benzaldehyde (10 g, 70 mmol) was dissolved in DMF (150 mL) and trichloroacetic acid (20.2 g, 123 mmol) was added. Addition of the sodium trichloroacetate (22.5 g, 121 mmol) was initiated at 21° C. All sodium trichloroacetate was added in portions within 30 min, the temperature was kept at 23-27° C. throughout the whole reaction. One hour later the aldehyde was consumed. The reaction mixture was stirred over night at room temperature. The mixture was cooled to 2° C. and acetic anhydride (20 mL, 211 mmol) was added dropwise within 1 h. During the addition the mixture became very thick and more DMF (400 mL) was added. After addition the mixture was warmed to room temperature during 1 h. Water was added to give a solution that was extracted three times with diethyl ether. The combined organic phase washed five times with water, dried (MgSO$_4$), filtered and evaporated to give the title compound as an yellow oil. Yield 84%, 18.2 g.

$^1$H NMR (500 MHz, CDCl$_3$): δ (ppm) 7.34-7.39 (m, 1H), 7.03-7.10 (m, 2H), 6.68 (s, 1H), 2.20 (s, 3H).

In a similar manner the following compounds were synthesized.

| 36.2 | 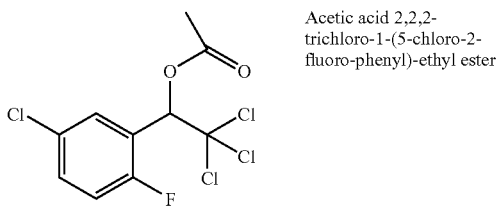 | Acetic acid 2,2,2-trichloro-1-(5-chloro-2-fluoro-phenyl)-ethyl ester | 83% |

¹H NMR (500 MHz, CDCl₃): δ (ppm) 7.66 (m, 1H), 7.38 (m, 1H), 7.07 (t, 1H), 6.70 (s, 1H), 2.23 (s, 3H)

| 36.3 | 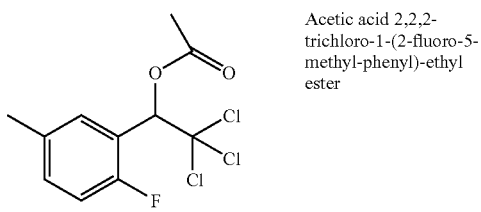 | Acetic acid 2,2,2-trichloro-1-(2-fluoro-5-methyl-phenyl)-ethyl ester | 84% |

¹H NMR (500 MHz, CDCl₃): δ (ppm) 7.44 (m, 1H), 7.17 (m, 1H), 6.96 (m, 1H), 6.70 (s, 1H), 2.34 (s, 3H), 2.19 (s, 3H).

Example 37.1

2-(2,2-Dichloro-vinyl)-1,4-difluoro-benzene

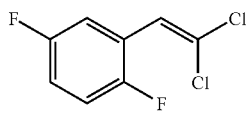

The title compound of Example 36.1 (18.2 g, 59 mmol) was dissolved in acetic acid (95 mL) in a 500 mL two neck flask. Zinc powder (7.6 g, 116 mmol) was added in one portion. The temperature of the mixture reached 60° C. The reaction was complete after 30 min. The mixture was filtered and pentane (200 mL) and water (200 mL) were added. The phases were separated and the water phase washed once again with pentane. The organic phases were combined and washed with sodium hydrogen carbonate solution until pH was neutral, dried (MgSO₄), filtered and concentration on reduced-pressure evaporator to give a yellow oil. Yield 82%, 10.2 g.

¹H NMR (500 MHz, CDCl₃): δ 7.49-7.55 (m, 1H), 6.95-7.04 (m, 2H), 6.93 (s, 1H).

In a similar manner the following compounds were synthesized.

| 37.2 | 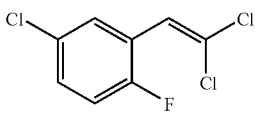 | 4-Chloro-2-(2,2-dichloro-vinyl)-1-fluoro-benzene | 90% |

¹H NMR (500 MHz, CDCl₃): δ (ppm) 7.77 (m, 1H), 7.27 (m, 1H), 7.02 (t, 1H), 6.92 (s, 1H)

| 37.3 | 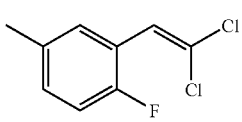 | 2-(2,2-Dichloro-vinyl)-1-fluoro-4-methyl-benzene | 93% |

¹H NMR (500 MHz, CDCl₃): δ (ppm) 7.53 (m, 1H), 7.07 (m, 1H), 6.93 (m, 2H), 2.32 (s, 3H).

Example 38.1

2-Ethynyl-1,4-difluoro-benzene

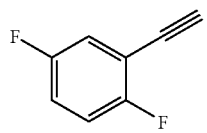

The title compound of Example 37.1 (10.2 g, 48.7 mmol) was dissolved in dry THF (63 mL), cooled on a dry ice/isopropanol bath to −55° C. and butyl lithium (2.5 M, 42 mL, 105 mmol) was added within 30 min at a rate that kept the temperature below −40° C. LC/MS showed good conversion 20 min after the addition of BuLi and stirring. The mixture was warmed up to 0° C. with the aid of a water bath. At 0° C. the mixture was quenched with potassium hydrogen sulfate (2 M solution) until a neutral aqueous phase was achieved. Diethyl ether was added and the water phase was extracted twice with a small amount of diethyl ether. The organic phases were combined and dried ($MgSO_4$), filtered and carefully evaporated using only heat. The solvent was removed by distillation under normal air pressure with the oil bath temperature at 80° C. The remaining residue was distilled in vacuo, and the fraction at 30° C./0 mmHg was collected. Yield 51%, 3.8 g.

$^1$H NMR (500 MHz, $CDCl_3$): δ (ppm) 7.12-7.17 (m, 1H), 6.99-7.03 (m, 2H), 3.31 (s, 1H).

In a similar manner the following compounds were synthesized.

| 38.2 | ![] | 4-Chloro-2-ethynyl-1-fluoro-benzene | 56% |
|---|---|---|---|
| $^1$H NMR | (500 MHz, $CDCl_3$): δ (ppm) 7.47 (m, 1H), 7.29 (m, 1H), 7.03 (m, 1H), 3.34 (s, 1H) | | |
| 38.3 | ![] | 2-Ethynyl-1-fluoro-4-methyl-benzene | 76% |
| $^1$H NMR | (500 MHz, $CDCl_3$): δ (ppm) 7.25 (m, 1H), 7.09 (m, 1H), 6.93 (m, 1H), 3.24 (s, 1H), 2.27 (s, 3H) | | |

Biological Evaluation

Functional Assessment of mGluR5 Antagonism in Cell Lines Expressing mGluR5D The properties of the compounds of the invention can be analyzed using standard assays for pharmacological activity. Examples of glutamate receptor assays are well known in the art as described in for example Aramori et al., *Neuron* 8:757 (1992), Tanabe et al., *Neuron* 8:169 (1992), Miller et al., *J. Neuroscience* 15: 6103 (1995), Balazs, et al., *J. Neurochemistry* 69:151 (1997). The methodology described in these publications is incorporated herein by reference. Conveniently, the compounds of the invention can be studied by means of an assay (FLIPR) that measures the mobilization of intracellular calcium, $[Ca^{2+}]_i$ in cells expressing mGluR5 or another assay (IP3) that measures inositol phosphate turnover.

FLIPR Assay

Cells expressing human mGluR5d as described in WO97/05252 are seeded at a density of 100,000 cells per well on collagen coated clear bottom 96-well plates with black sides and experiments are done 24 h following seeding. All assays are done in a buffer containing 127 mM NaCl, 5 mM KCl, 2 mM $MgCl_2$, 0.7 mM $NaH_2PO_4$, 2 mM $CaCl_2$, 0.422 mg/mL $NaHCO_3$, 2.4 mg/mL HEPES, 1.8 mg/mL glucose and 1 mg/mL BSA Fraction IV (pH 7.4). Cell cultures in the 96-well plates are loaded for 60 minutes in the above mentioned buffer containing 4 μM of the acetoxymethyl ester form of the fluorescent calcium indicator fluo-3 (Molecular Probes, Eugene, Oreg.) in 0.01% pluronic acid (a proprietary, non-ionic surfactant polyol—CAS Number 9003-11-6). Following the loading period the fluo-3 buffer is removed and replaced with fresh assay buffer. FLIPR experiments are done using a laser setting of 0.800 W and a 0.4 second CCD camera shutter speed with excitation and emission wavelengths of 488 nm and 562 nm, respectively. Each experiment is initiated with 160 μl of buffer present in each well of the cell plate. A 40 μl addition from the antagonist plate was followed by a 50 μL addition from the agonist plate. A 30 minute interval separates the antagonist and agonist additions. The fluorescence signal is sampled 50 times at 1 second intervals followed by 3 samples at 5 second intervals immediately after each of the two additions. Responses are measured as the difference between the peak height of the response to agonist, less the background fluorescence within the sample period. $IC_{50}$ determinations are made using a linear least squares fitting program.

IP3 Assay

An additional functional assay for mGluR5d is described in WO97/05252 and is based on phosphatidylinositol turnover. Receptor activation stimulates phospholipase C activity and leads to increased formation of inositol 1,4,5,triphosphate ($IP_3$). GHEK stably expressing the human mGluR5d are seeded onto 24 well poly-L-lysine coated plates at $40 \times 10^4$ cells/well in media containing 1 μCi/well [3H] myo-inositol. Cells were incubated overnight (16 h), then washed three times and incubated for 1 h at 37° C. in HEPES buffered saline (146 mM NaCl, 4.2 mM KCl, 0.5 mM $MgCl_2$, 0.1% glucose, 20 mM HEPES, pH 7.4) supplemented with 1 unit/mL glutamate pyruvate transaminase and 2 mM pyruvate. Cells are washed once in HEPES buffered saline and pre-incubated for 10 min in HEPES buffered saline containing 10 mM LiCl. Compounds are incubated in duplicate at 37° C. for 15 min, then either glutamate (80 μM) or DHPG (30 μM) is added and incubated for an additional 30 min. The reaction is terminated by the addition of 0.5 mL perchloric acid (5%) on ice, with incubation at 4° C. for at least 30 min. Samples are collected in 15 mL polypropylene tubes and inositol phosphates are separated using ion-exchange resin (Dowex AG1-X8 formate form, 200-400 mesh, BIORAD) columns. Inositol phosphate separation was done by first eluting glycero phosphatidyl inositol with 8 mL 30 mM ammonium formate. Next, total inositol phosphates is eluted with 8 mL 700 mM ammonium formate/100 mM formic acid and collected in scintillation vials. This eluate is then mixed with 8 mL of scintillant and [3H] inositol incorporation is determined by scintillation counting. The dpm counts from the duplicate samples are plotted and $IC_{50}$ determinations are generated using a linear least squares fitting program.

Abbreviations
BSA Bovine Serum Albumin
CCD Charge Coupled Device
CRC Concentration Response Curve
DHPG 3,5-dihydroxyphenylglycine
DPM Disintegrations per Minute
EDTA Ethylene Diamine Tetraacetic Acid
FLIPR Fluorometric Imaging Plate reader
GHEK GLAST-containing Human Embrionic Kidney
GLAST glutamate/aspartate transporter
HEPES 4-(2-hydroxyethyl)-1-piperazineethanesulfonic acid (buffer)
$IP_3$ inositol triphosphate Generally, the compounds were active in the assay above with $IC_{50}$ values less than 10 000 is nM. In one aspect of the invention, the $IC_{50}$ value is less than 1 000 nM. In a further aspect of the invention, the $IC_{50}$ value is less than 100 nM.

Determination of Brain to Plasma Ratio in Rat

Brain to plasma ratios are estimated in female Sprague Dawley rats. The compound is dissolved in water or another appropriate vehicle. For determination of brain to plasma ratio the compound is administrated as a subcutaneous, or an intravenous bolus injection, or an intravenous infusion, or an oral administration. At a predetermined time point after the administration a blood sample is taken with cardiac puncture. The rat is terminated by cutting the heart open, and the brain is immediately retained. The blood samples are collected in heparinized tubes and centrifuged within 30 minutes, in order to separate the plasma from the blood cells. The plasma is transferred to 96-well plates and stored at −20° C. until analysis. The brains are divided in half, and each half is placed in a pre-tarred tube and stored at −20° C. until analysis. Prior to the analysis, the brain samples are thawed and 3 mL/g brain tissue of distilled water is added to the tubes. The brain samples are sonicated in an ice bath until the samples are homogenized. Both brain and plasma samples are precipitated with acetonitrile. After centrifugation, the supernatant is diluted with 0.2% formic acid. Analysis is performed on a short reversed-phase HPLC column with rapid gradient elution and MSMS detection using a triple quadrupole instrument with electrospray ionisation and Selected Reaction Monitoring (SRM) acquisition. Liquid-liquid extraction may be used as an alternative sample clean-up. The samples are extracted, by shaking, to an organic solvent after addition of a suitable buffer. An aliquot of the organic layer is transferred to a new vial and evaporated to dryness under a stream of nitrogen. After reconstitution of the residuals the samples are ready for injection onto the HPLC column.

Generally, the compounds according to the present invention are peripherally restricted with a drug in brain over drug in plasma ratio in the rat of <0.5. In one embodiment, the ratio is less than 0.15.

Determination of In vitro Stability

Rat liver microsomes are prepared from Sprague-Dawley rats liver samples. Human liver microsomes are either prepared from human liver samples or acquired from BD Gentest. The compounds are incubated at 37° C. at a total microsome protein concentration of 0.5 mg/mL in a 0.1 mol/L potassium phosphate buffer at pH 7.4, in the presence of the cofactor, NADPH (1.0 mmol/L). The initial concentration of compound is 1.0 µmol/L. Samples are taken for analysis at 5 time points, 0, 7, 15, 20 and 30 minutes after the start of the incubation. The enzymatic activity in the collected sample is immediately stopped by adding a 3.5 times volume of acetonitrile. The concentration of compound remaining in each of the collected samples is determined by means of LC-MS. The elimination rate constant (k) of the mGluR5 inhibitor is calculated as the slope of the plot of ln[mGluR5 inhibitor] against incubation time (minutes). The elimination rate constant is then used to calculate the half-life (T ½) of the mGluR5 inhibitor, which is subsequently used to calculate the intrinsic clearance (CLint) of the mGluR5 inhibitor in liver microsomes as: CLint.=(ln 2×incubation volume)/(T ½×protein concentration)=µl/min/mg Screening for Compounds Active Against TLESR Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 mL/kg) in a foreleg vein. Ten min after i.v. administration, a nutrient meal (10% peptone, 5% D-glucose, 5% Intralipid, pH 3.0) is infused into the stomach through the central lumen of the assembly at 100 mL/min to a final volume of 30 mL/kg. The infusion of the nutrient meal is followed by air infusion at a rate of 500 mL/min until an intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal ≦2 s before its onset in which case the relaxation is classified as swallow-induced. The pressure difference between the LES and the stomach should be less than 2 mmHg, and the duration of the complete relaxation longer than 1 s.

Specimen Results are Shown in the Following Table:

| Example | FLIPR hmGluR5d (nM) | Brain/Plasma Ratio of compound in Rat | HERG ionworks (µM) | Clint (human) (µL/min/mg) |
|---|---|---|---|---|
| 31.7 | 47 | 0.005 | 23 | <12 |
| 31.8 | 25 | 0.11 | 16 | <12 |
| 31.11 | 39 | 0.035 | 20 | <12 |
| 31.19 | 50 | 0.01 | 24 | <12 |

The invention claimed is:
1. A compound of formula (I)
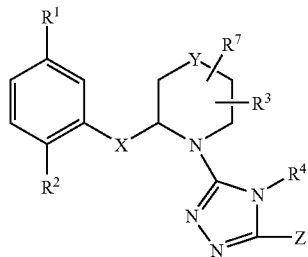
wherein
$R^1$ is methyl, halogen or cyano;
$R^2$ is hydrogen or fluoro;
$R^3$ is hydrogen, fluoro or $C_1$-$C_3$ alkyl;
$R^4$ is $C_1$-$C_3$ alkyl or cyclopropyl;
Y is a bond;
X is
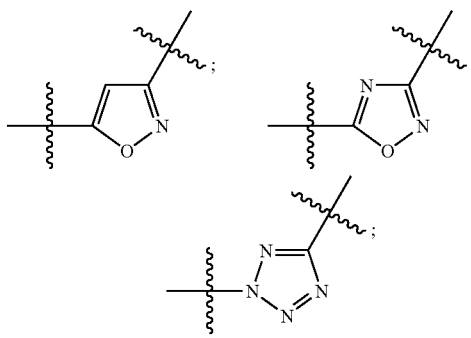
or
and Z is
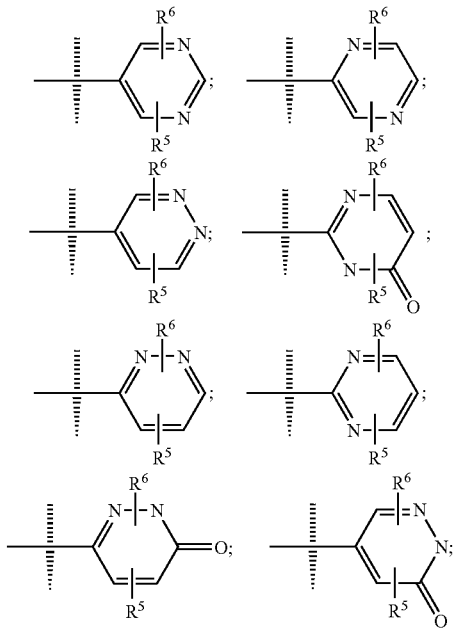
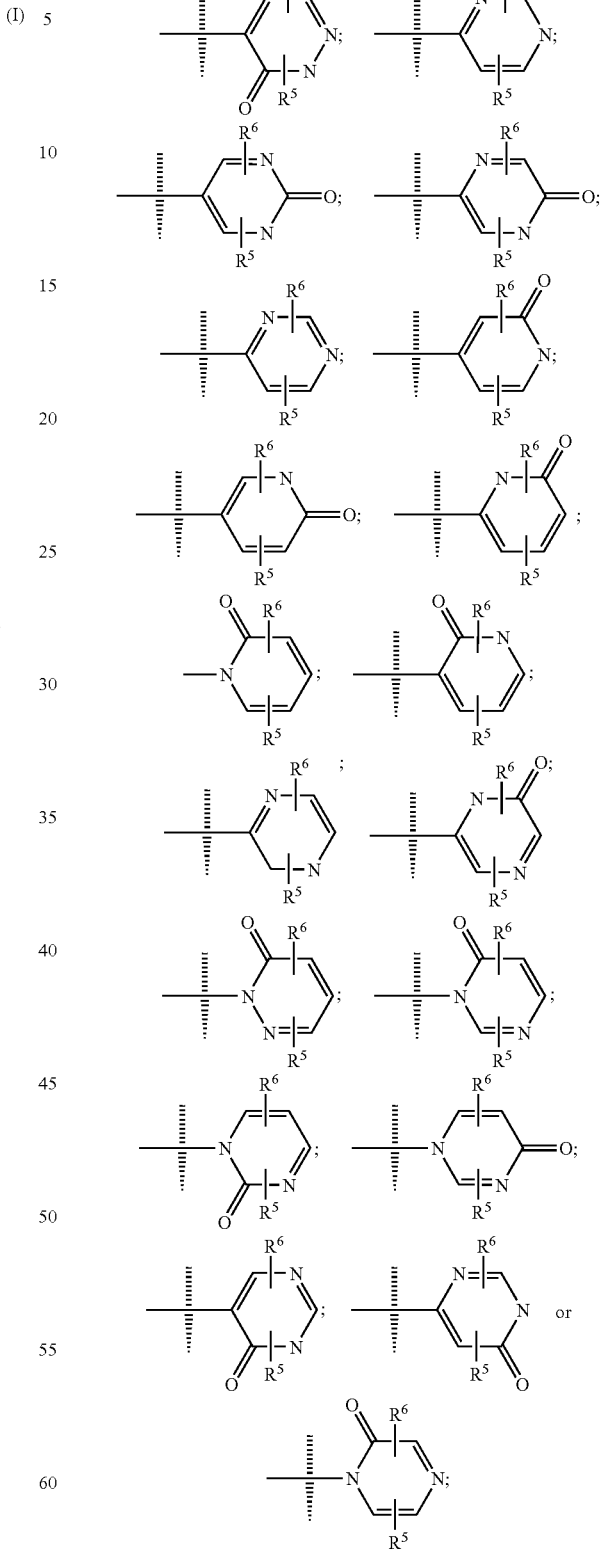
wherein
$R^5$ is hydrogen, $C_1$-$C_3$ alkyl, $C_1$-$C_3$ haloalkyl, $C_1$-$C_3$ alkoxy; $C_1$-$C_3$ haloalkoxy; or halogen;

$R^6$ is hydrogen, $C_1$-$C_3$ alkyl, $C_1$-$C_3$ haloalkyl, $C_1$-$C_3$ alkoxy; $C_1$-$C_3$ haloalkoxy; or halogen;

$R^7$ is hydrogen, fluoro or $C_1$-$C_3$ alkyl;

as well as pharmaceutically acceptable salts, tautomers and/or enantiomers thereof.

2. A compound according to claim 1, wherein $R^1$ is halogen or cyano.

3. A compound according to claim 2, wherein $R^1$ is chloro.

4. A compound according to claim 2, wherein $R^1$ is fluoro.

5. A compound according to claim 2, wherein $R^1$ is methyl.

6. A compound according to claim 2, wherein $R^1$ is cyano.

7. A compound according to claim 1, wherein $R^2$ is hydrogen.

8. A compound according to claim 1, wherein $R^3$ is hydrogen or fluoro.

9. A compound according to claim 1, wherein $R^4$ is $C_1$-$C_2$ alkyl.

10. A compound according to claim 9, wherein $R^4$ is methyl.

11. A compound according to claim 1, wherein $R^5$ is hydrogen, $C_1$-$C_2$ alkyl or $C_1$-$C_2$ alkoxy.

12. A compound according to claim 1, wherein $R^6$ is hydrogen, $C_1$-$C_2$ alkyl or $C_1$-$C_2$ alkoxy.

13. A compound according to claim 1, wherein $R^7$ is hydrogen or fluoro.

14. A compound according to claim 1, wherein Z is

15. A compound according to claim 14, wherein Z is

16. A compound according to claim 14, wherein Z is

17. A compound according to claim 14, wherein Z is

18. A compound selected from;

3-{3-[(R)-1-(4-Methyl-5-pyrimidin-5-yl-4H-[1,2,4]triazol-3-yl)-pyrrolidin-2-yl]-isoxazol-5-yl}-benzonitrile;

3-{5-[(R)-1-(4-Methyl-5-pyrazin-2-yl-4H-[1,2,4]triazol-3-yl)-pyrrolidin-2-yl]-tetrazol-2-yl}-benzonitrile;

3-{3-[(R)-1-(4-Methyl-5-pyrazin-2-yl-4H-[1,2,4]triazol-3-yl)-pyrrolidin-2-yl]-isoxazol-5-yl}-benzonitrile;

5-(5-{(R)-2-[2-(3-Chloro-phenyl)-2H-tetrazol-5-yl]-pyrrolidin-1-yl}-4-methyl-4H-[1,2,4]triazol-3-yl)-pyrimidine;

4-(5-{(R)-2-[5-(3-Chloro-phenyl)-isoxazol-3-yl]-pyrrolidin-1-yl}-4-methyl-4H-[1,2,4]triazol-3-yl)-1-methyl-1H-pyridin-2-one;

5-(5-{(R)-2-[5-(3-Chloro-phenyl)-isoxazol-3-yl]-pyrrolidin-1-yl}-4-methyl-4H-[1,2,4]triazol-3-yl)-1-methyl-1H-pyridin-2-one;

4-(5-{(R)-2-[5-(3-Chloro-phenyl)-isoxazol-3-yl]-pyrrolidin-1-yl}-4-methyl-4H-[1,2,4]triazol-3-yl)-pyridazine;

(+/−)5-(5-{2-[5-(3-Chloro-phenyl)-isoxazol-3-yl]-pyrrolidin-1-yl}-4-methyl-4H-[1,2,4]triazol-3-yl)-pyrimidine;

2-(5-{(S)-2-[5-(3-Chloro-phenyl)-isoxazol-3-yl]-pyrrolidin-1-yl}-4-methyl-4H-[1,2,4]triazol-3-yl)-pyrazine;

4-(5-{(R)-2-[2-(3-Chloro-phenyl)-2H-tetrazol-5-yl]-pyrrolidin-1-yl}-4-methyl-4H-[1,2,4]triazol-3-yl)-1-methyl-1H-pyridin-2-one;

4-(5-{(R)-2-[2-(3-Chloro-phenyl)-2H-tetrazol-5-yl]-pyrrolidin-1-yl}-4-methyl-4H-[1,2,4]triazol-3-yl)-1H-pyridin-2-one;

4-(5-{(R)-2-[5-(3-Chloro-phenyl)-isoxazol-3-yl]-pyrrolidin-1-yl}-4-methyl-4H-[1,2,4]triazol-3-yl)-1H-pyridin-2-one;

6-(5-{(R)-2-[5-(3-Chloro-phenyl)-isoxazol-3-yl]-pyrrolidin-1-yl}-4-methyl-4H-[1,2,4]triazol-3-yl)-2-methyl-2H-pyridazin-3-one;

5-(5-{(R)-2-[5-(3-Chloro-phenyl)-isoxazol-3-yl]-pyrrolidin-1-yl}-4-methyl-4H-[1,2,4]triazol-3-yl)-2H-pyridazin-3-one;
5-(5-{(R)-2-[5-(3-Fluoro-phenyl)-isoxazol-3-yl]-pyrrolidin-1-yl}-4-methyl-4H-[1,2,4]triazol-3-yl)-2H-pyridazin-3-one;
6-(5-{(R)-2-[5-(3-Fluoro-phenyl)-isoxazol-3-yl]-pyrrolidin-1-yl}-4-methyl-4H-[1,2,4]triazol-3-yl)-2-methyl-2H-pyridazin-3-one;
1-Methyl-4-{4-methyl-5-[(R)-2-(5-m-tolylisoxazol-3-yl)pyrrolidin-1-yl]-4H-[1,2,4]triazol-3-yl}-1H-pyridin-2-one;
5-{4-Methyl-5-[(R)-2-(5-m-tolyl-isoxazol-3-yl)-pyrrolidin-1-yl]-4H-[1,2,4]triazol-3-yl}-2H-pyridazin-3-one;
4-(5-{(R)-2-[5-(3-Fluoro-phenyl)-isoxazol-3-yl]-pyrrolidin-1-yl}-4-methyl-4H-[1,2,4]triazol-3-yl)-1H-pyridin-2-one;
2-Methyl-5-{4-methyl-5-[(R)-2-(5-m-tolyl-isoxazol-3-yl)-pyrrolidin-1-yl]-4H-[1,2,4]triazol-3-yl}-2H-pyridazin-3-one;
4-(5-{(R)-2-[5-(3-Chloro-phenyl)-isoxazol-3-yl]-pyrrolidin-1-yl}-4-methyl-4H-[1,2,4]triazol-3-yl)-1,6-dimethyl-1H-pyridin-2-one;
4-{4-Methyl-5-[(R)-2-(5-m-tolyl-isoxazol-3-yl)-pyrrolidin-1-yl]-4H-[1,2,4]triazol-3-yl}-1H-pyridin-2-one;
6-{4-Methyl-5-[(R)-2-(5-m-tolyl-isoxazol-3-yl)-pyrrolidin-1-yl]-4H-[1,2,4]triazol-3-yl}-3H-pyrimidin-4-one;
4-(5-{(R)-2-[2-(3-Chloro-phenyl)-2H-tetrazol-5-yl]-pyrrolidin-1-yl}-4-methyl-4H-[1,2,4]triazol-3-yl)-pyridazine;
5-(5-{(R)-2-[5-(3-Chlorophenyl)isoxazol-3-yl]-pyrrolidin-1-yl}-4-methyl-4H-[1,2,4]triazol-3-yl)-2-methyl-2H-pyridazin-3-one;
5-(5-{(R)-2-[5-(3-Fluorophenyl)isoxazol-3-yl]-pyrrolidin-1-yl}-4-methyl-4H-[1,2,4]triazol-3-yl)-2-methyl-2H-pyridazin-3-one;
6-(5-{(R)-2-[5-(3-Chlorophenyl)isoxazol-3-yl]-pyrrolidin-1-yl}-4-methyl-4H-[1,2,4]triazol-3-yl)-3H-pyrimidin-4-one;
6-(5-{(R)-2-[5-(3-Chloro-phenyl)-isoxazol-3-yl]-pyrrolidin-1-yl}-4-methyl-4H-[1,2,4]triazol-3-yl)-1H-pyridin-2-one
5-(5-{(R)-2-[5-(2,5-Difluoro-phenyl)-isoxazol-3-yl]-pyrrolidin-1-yl}-4-methyl-4H-[1,2,4]triazol-3-yl)-2H-pyridazin-3-one;
6-(5-{(R)-2-[5-(5-Chloro-2-fluoro-phenyl)-isoxazol-3-yl]-pyrrolidin-1-yl}-4-methyl-4H-1,2,4-triazol-3-yl)-3H-pyrimidin-4-one;
4-(5-{(R)-2-[5-(5-Chloro-2-fluoro-phenyl)-isoxazol-3-yl]-pyrrolidin-1-yl}-4-methyl-4H-[1,2,4]triazol-3-yl)-1H-pyridin-2-one;
5-(5-{(R)-2-[5-(5-Chloro-2-fluoro-phenyl)-isoxazol-3-yl]-pyrrolidin-1-yl}-4-methyl-4H-[1,2,4]triazol-3-yl)-2H-pyridazin-3-one;
4-(5-{(R)-2-[5-(2-Fluoro-5-methyl-phenyl)-isoxazol-3-yl]-pyrrolidin-1-yl}-4-methyl-4H-[1,2,4]triazol-3-yl)-1H-pyridin-2-one; and as well as pharmaceutically acceptable salts, tautomers and/or enantiomers thereof.

19. A pharmaceutical composition comprising a compound according to claim 1 as an active ingredient, together with a pharmacologically and pharmaceutically acceptable carrier.

20. A combination comprising (i) at least one compound according to claim 1 and (ii) at least one acid secretion inhibiting agent.

21. A combination according to claim 20 wherein the acid secretion inhibiting agent is selected from cimetidine, ranitidine, omeprazole, esomeprazole, lansoprazole, pantoprazole, rabeprazole or leminoprazole.

* * * * *